(12) United States Patent
Freeman

(10) Patent No.: US 7,718,391 B2
(45) Date of Patent: *May 18, 2010

(54) ASSAYS FOR IDENTIFYING MODULATORS OF RHOMBOID POLYPEPTIDES

(75) Inventor: Matthew Freeman, Cambridge (GB)

(73) Assignee: Medical Research Council, London (GB)

( * ) Notice: Subject to any disclaimer, the term of this patent is extended or adjusted under 35 U.S.C. 154(b) by 473 days.

This patent is subject to a terminal disclaimer.

(21) Appl. No.: 10/477,505

(22) PCT Filed: May 13, 2002

(86) PCT No.: PCT/GB02/02234

§ 371 (c)(1), (2), (4) Date: Jul. 26, 2004

(87) PCT Pub. No.: WO02/093177

PCT Pub. Date: Nov. 21, 2002

(65) Prior Publication Data

US 2005/0142546 A1 Jun. 30, 2005

(30) Foreign Application Priority Data

May 11, 2001 (GB) ................................. 0111574.0
Sep. 27, 2001 (GB) ................................. 0123261.0

(51) Int. Cl.
C12Q 1/37 (2006.01)
A01N 1/02 (2006.01)

(52) U.S. Cl. ........................................... 435/23; 435/4

(58) Field of Classification Search .................. 435/23, 435/4

See application file for complete search history.

(56) References Cited

U.S. PATENT DOCUMENTS 5,712,143 A * 1/1998 Grieve et al. ................ 435/212
6,924,117 B2 * 8/2005 Lioubin et al. ............. 435/7.23
2002/0102604 A1 * 8/2002 Milne Edwards et al. .... 435/7.1
2006/0127968 A1 * 6/2006 Freeman ....................... 435/32

FOREIGN PATENT DOCUMENTS

WO     WO 0136659 A2 * 5/2001
WO     WO 02/05843      1/2002

OTHER PUBLICATIONS

Gupta S, Maiden MC. Exploring the evolution of diversity in pathogen populations. Trends Microbiol. Apr. 2001;9(4):181-5.*
Gallio M, Kylsten P.,Providencia may help find a function for a novel, widespread protein family. Curr. Biol. Oct. 5, 2000;10(19):R693-4.*
Urban S. Rhomboid proteins: conserved membrane proteases with divergent biological functions.Genes & development, 2006 vol. 20: 3054-3068.*
Miller MB, Bassler BL.,Quorum sensing in bacteria. Annual Review of Microbiology 2001;55:165-99.*
Bang et al., "Rhomboid and Star facilitate presentation and processing of the *Drosophiila* TGF-α homolog Spitz," Genes & Dev., 2000, 14:177-186.
Guichard et al., brother of rhomboid, a rhomboid-Related Gene Expressed during Early *Drosophila* Oogenesis, Promotes EGF-R/MAPK Signaling, Dev. Biology, 2000, 226: 255-266.
Pascall et al., Characterization of a mammalian cDNA encoding a protein with high sequence similarity to the *Drosophila* regulatory protein Rhomboid, FEBS, 1998, 429: 337-340.
Urban et al., "*Drosophila* Rhomboid-1 Defines a Family of Putative Intramembrane Serine Proteases," Cell, 2001, 107: 173-182. XP-002219149.
Wasserman; et al., "A family of rhomboid-like genes: *Drosophila* rhomboid-1 and roughoid/rhomboid-3 cooperate to activate EGF receptor signaling", Genes & Development (2000), 14:1651-1663.

* cited by examiner

*Primary Examiner*—Maria Leavitt
(74) *Attorney, Agent, or Firm*—Bozicevic, Field & Francis LLP; Pamela J. Sherwood

(57) ABSTRACT

The present invention relates to proteins of the conserved Rhomboid family, which are involved in various signalling pathways within cells. Rhomboid proteins are found to possess a novel serine protease activity which cleaves within the transmembrane domain of a polypeptide substrate. Methods and uses of this activity are provided.

12 Claims, 12 Drawing Sheets

Figure 5

[Figure 5: Multiple sequence alignment of RHBDL1, RHBDL3, RHBDL2, and Rhomboid-1 proteins, showing conserved regions including the GXSGG motif. RHBDL3 predicted cDNA region is indicated.]

atgggcgagcaccccagcccgggccccgcggtggccgcctgcgccgaggcggagcgcat
⇩
cgaggagctggaacccgaggccgaggagcggctgcccgcggcgccggaggacGGTGGGG AGATGGAAGTGAAACCAGGCCCCCAACCCACACAACGAAAGCGGGAAAGTCTGAATGGG
⇩                                                    ⇩
GTTGGGGGGctggggaaggagccccagatggcagcaatacaaagagagaatctgTTTGA

CCCTGGGAACACAGGCTACATTAGCACAGGCAAGTTCCGGAGTCTTCTGGAGAGCCACA

GCTCCAAGCTGGACCCGCACAAAAGGGAGGTCCTCCTGGCTCTTGCCGACAGCCACGCG
⇩
GATGGCAGATCGGCTACCAGGATTTTGTCAGCCTAatgagcaacaagcgttccaacag cttccgccaagccatcctgcagggcaaccgcaggctaagcagcaaggccctgctggagg cgaaggggctgagcctctcgcagcgacttatccgccatgtggcctatgagaccctgccc cgggaaattgaccgcaagtggtactatgacagctacacctgctgcccccaccctggtt
⇩
catgatcacagtcacgctgctggaggcaaggacaagggtgGCCTTTTTCCTCTACAATG

GGGTGTCACTAGGTCAATTTGTACTGCAGGTAACTCATCCACGTTACTTGAAGAACTCC

CTGGTTTACCACCCACAGCTGCGAGCACAGGTTTGGCGCTACCTGACATACATCTTCAT
⇩
GCATGCAGGGatagaacacctgggactcaatgtggtgctgcagctgctggtgggggtgc ccctggagatggtgcatggagccacccgaattgggcttgtctacgtggccggtgttgtg
⇩
gcaggtTCCTTGGCAGTGTCTGTGGCTGACATGACCGCTCCAGTCGTGGGCTCTTCTGG
⇩
AGGGGTGTATGCTCTCGTCTCTGCCCATCTGGCCAACATTGTCATGaactggtcaggca
⇩
tgaagtgccagttcaagctgctgcggatggctgtggcccttatctgtGTGAGCATGGAG

TTTGGCGGGCCGTGTGGCTCCGCTTCCACCCGTCGGCCTATCCCCCGTGCCCTCACCC

AAGCTTTGTGGCGCACTTGGGTGGCGTGGCCGTGGGCATCACCCTGGGCGTGGTGGTCC

TGAGGAACTACGAGCAGAGGCTCCAGGACCAGTCACTGTGGTGGATTTTTGTGGCCATG

TACACCGTCTTCGTGCTGTTCGCTGTCTTCTGGAACATCTTTGCCTACACCCTGCTGGA

CTTAAAGCTGCCGCCTCCCCCC         ESTBE778475
────────────────────▶

Figure 7

MGEHPSPGPAVAACAEAERIEELEPEAEERLPAAPEDGGEMEVKPGPQPTQRKRESL
NGVGGLGKEPQMAAIQRENLFDPGNTGYISTGKFRSLLESHSSKLDPHKREVLLALA
DSHADGQIGYQDFVSLMSNKRSNSFRQAILQGNRRLSSKALLEEKGLSLSQRLIRHV
AYETLPREIDRKWYYDSYTCCPPPWFMITVTLLEARTRVAFFLYNGVSLGQFVLQVT
HPRYLKNSLVYHPQLRAQVWRYLTYIFMHAGIEHLGLNVVLQLLVGVPLEMVHGA
TRIGLVYVAGVVAGSLAVSVADMTAPVVGSSGGVYALVSAHLANIVMNWSGMKC
QFKLLRMAVALICMSMEFGRAVWLRFHPSAYPPCPHPSFVAHLGGVAVGITLGVV
LRNYEQRLQDQSLWWIFVAMYTVFVLFAVFWNIFAYTLLDLKLPPPP

Figure 8

```
CACTGTTGGCCTACTGGGATGCCCCGCTAACAAATTCATGAATGGGAGTGAAGCAACGCTAC
TGACGCAGATAGAGAAATGGGCGATAATGACACCGAAGAGCAAGACTCTTTGCAGAAGAAGG
ACGAAGAAGCTGGTAACCGAGACAATCCGGTCAGAAGAGTTCGGAGGGTCGAGAAGTTTCAT
AAGAATGTTTCTAAATGGATGCTTCCCGAGGAGTTACATGAGACTTATCTTGAGCGGGCGAA
CTGCTGTCCGCCACCGATCTTCATCATCCTCATCAGTTTAGCAGAGCTGGCCGTGTTTATCT
ACTACGCTGTATGGAAGCCTCAAAAACAGTGGATAACTCTAGGAACTGGGATCTGGGATAGT
CCTCTTACCTATAGGCCAGAACAACGCAAGGAGGCTTGGCGCTTTGTTTCCTACATGTTTGT
ACATGCCGGGGTGGAGCATATCATGGGGAACCTATTAATGCAGCTTCTTCTGGGTATTCCTC
TGGAACTGGTCCATAAAGGCTTTGAAGTTGGCATGGTGTACATGTGTGGGGTCCTCGCAGGG
TCTCTGGCCAGCTCCATCTTTGATCCTTTCAGTGCTCTTGTGGGAGCTTCAGGTGGTGTTTA
TGCCCTTATGGGTGGCTACTTCATGAATGCCATTGTGAATTTCCGGGAGATGAGAGTTCTTC
TAGGAGTGTTTCGCATCTTAGTGATTGTTTTGATTGTTGGAACAGATGTTGGATTTGCTCTT
TATAGAAGGTTCATTGTCCACGAGGCTGGCCTAAAGGTCTCTTTTGTGGCTCATATTGGCGG
TGGCATAGCAGGCATGACCATTGGTTATGTGTTTTTCACCAACTACAATAAAGAGCTTCTAA
AAGACCCACGCTTCTGGATGTGCATTGTGGGATACATCGTCTTCTTACTGTTTGCAGTCATT
TTCAACATCTTCTTGTCCCCAGCACCCGCATGAGGTCATCAATGGACAGTCGAACCTTTTTT
TTATTTTATAAAAGAATGAGGTCAACACAACTGTCAGACAATCCTGTTGGTATTTATAGACT
CATAAAGGGTTAGTTCAACTGAAAACTCTGTATTGACCCATATTGTTCTTTCAGAAGTTCAT
CTTTGAAACACAAATGAAGATATTTTTAAATCAAGCCGAGCGATTTCGTTTCTTCTATTCAG
AGTCTGTTTACCCTACACCTTTGACTATGAAAGGATCAGAATCCATATAAATAGGTTCACAT
TTTATGAATGAATAGATTTAATTTTGGTTTACATTTCAGAAATTTGGATTTGGAAATCTTTA
GGGTTTCATTAAAAGTATCCTAATTTGTGTATTGAAGATGGGAAGATTTCTTATGGGTTTGG
AATGGGATGAGGGAGTCTATTTACATTTTACACTGAACTAACCCTTTAGGAAATATGCTAAC
ACACTACAAGCACATCTAAAGAAAGTAACTGTCATATTTTGGATATTTTTAAATGTAATTT
```

Figure 10

```
TTTTTAATGTCATGTAATTTATGTTTTTTGTTTAGTTTTGTATTGTTTTGCTTAACACATGT

ACTTAAGTAATGTATTGCCTCAGGGGAAAAAATGATAAAGCATATATTTTTAATTGTTTGG

GTTTTACAAAATCATTGGGCATTTCTGGACTGGCCAACATTTTTAATTCATGACTAAACAGC

TTGGTTTATTTGAATTCAGTTCAATTTGTTTGGAGATAAATGCATTTAAAGTTCACCAAAAA

ATATAAATTCTATCATCATATATATACCCTTTACTTGTAACAAACCTTTCATTCTTCTGTTA

AACACAAAACAAGATATTGTGAAGAATTTTGAAAACCAGTAACCATCGACTTTCAAAGTACA

ACATTCTTTAAAACATCTTCATTCGTGTTTTAGAGAACGTTTTGTACTTAAAAGAAACTCA

TAAATTTTAGAAAACCCTTGAGGGTGAGGAATTTGTGAGTAAATTTTGATTTGAGGGTTAAC

TATCCCTTTAAAAAAAGAGGTTTCGTTTTGATACCAATAGAGGGCAGCATTGATCAGCATGT

GGGCATTGGAAGACACTGACCTATAAAAAGTAGGAAATTGTTAAATCAGTGCTAATGACATG

CATCTGTATTTACCCTACGTATTTGTCCCTAATTATCAAATCATTTATTTTCAGAAATGGGT

TTGGGTTTGGAATGTTTTGGCCATATAGAGGCCATATAGCCTTTTTTATTTTTTTTATGAAA

TAATAAAAAGAATTGTGCCAATGTTTT
```

Figure 10 continued

MGDNDTEEQDSLQKKDEEAGNRDNPVRRVRRVEKFHKNVSKWMLPEELHETYLERANCCPPP

IFIILISLAELAVFIYYAVWKPQKQWITLGTGIWDSPLTYRPEQRKEAWRFVSYMFVHAGVE

HIMGNLLMQLLLGIPLELVHKGFEVGMVYMCGVLAGSLASSIFDPFSALVGASGGVYALMGG

YFMNAIVNFREMRVLLGVFRILVIVLIVGTDVGFALYRRFIVHEAGLKVSFVAHIGGGIAGM

TIGYVFFTNYNKELLKDPRFWMCIVGYIVFLLFAVIFNIFLSPAPA

Figure 11

ASSAYS FOR IDENTIFYING MODULATORS OF RHOMBOID POLYPEPTIDES

The present invention relates to proteins of the Rhomboid family, which are conserved throughout evolution and which, in *Drosophila*, are involved in epidermal growth factor receptor signaling. In particular, the present invention relates to the activity and function of the members of this protein family.

Rhomboid-1 is a member of a group of seven related proteins in *Drosophila*, each with seven TMDs, and is the prototype of a family conserved throughout evolution (Wasserman et al., (2000) Genes Dev. 14, 1651-1663). Although no activity or function has been previously assigned to any member of this family, Rhomboid-1 appears to be the principal trigger of epidermal growth factor receptor (EGFR) activation in *Drosophila*.

EGF receptor tyrosine kinases regulate many cellular decisions in animal growth and development. *Drosophila* has a single EGF receptor, which is equally similar to all four of the mammalian ErbB receptors and probably represents their evolutionary prototype. Like its mammalian counterparts, the *Drosophila* EGF receptor has multiple functions during development, including control of differentiation, proliferation and cell survival (Schweitzer and Shilo,(1997) Trends in Genetics 13, 191-196; Dominguez et al., (1998) Current Biol. 8, 1039-1048).

The EGF receptor pathway has been well conserved between flies and mammals and components involved in the mechanism and control of mammalian ErbB signaling (Casci and Freeman, (1999) Cancer and Metastasis Rev. 18, 181-201) may be identified by *Drosophila* genetics. This is an important goal as not only do these receptors regulate many cellular functions in mammals, but their hyperactivity is also strongly implicated in human cancer and other diseases (Yarden and Sliwkowski, (2001) Nature Reviews Molecular and Cell Biology 2, 127-137).

The principal activating ligand of the *Drosophila* EGF receptor is Spitz, which is similar to mammalian TGFα and is synthesised with a single transmembrane domain (TMD) and one extracellular EGF domain (Rutledge et al.(1992) Genes Dev. 6, 1503-1517). Although genetic evidence has led to the suggestion that Spitz may be proteolytically cleaved to a soluble extracellular fragment in order to function as a ligand, this has not been shown biochemically (Freeman, 1994 Mech. Dev. 48, 25-33; Schweitzer et al., (1995) Genes Dev. 9, 1518-1529.; Golembo et al.(1996) Development 122, 3363-70).

Although Spitz was initially identified genetically, its molecular mechanism was strongly suggested by its similarity to known mammalian ligands. This is not true for other EGF receptor signaling components which have been discovered by fly genetics. For example, the transmembrane molecules Rhomboid-1 and Star are genetically defined as primary regulators of EGF receptor signaling in *Drosophila* but no function is suggested by their protein sequences.

Rhomboid-1 and its close homologue, Rhomboid-3, are required for EGF receptor activation; in many contexts they trigger ectopic activation of the pathway; and finally, the expression pattern of the rhomboid-1 gene prefigures receptor activity (Bier et al., (1990) Genes Dev. 4, 190-203; Freeman et al., (1992) Development 116, 335-346; Ruohola-Baker et al., (1993) Cell 73, 953-965.; Sturtevant et al., (1993) Genes Dev. 7, 961-973; Golembo et al., (1996) Development 122, 3363-70; zür Lage et al. (1997) Current Biology 7, 166-175; Wasserman and Freeman, (1998) Cell 95, 355-364; Guichard et al., (1999) Development 126, 2663-76; Wasserman et al., (2000) Genes Dev. 14, 1651-1663).

Similar results obtained with Star, a type 2 transmembrane protein with a single TMD (Kolodkin et al. (1994) Development 120, 1731-1745.), suggest that it also regulates EGF receptor signaling in most contexts. Genetic analysis indicates that Rhomboid-1 and Star both act in the signal-emitting cell (Heberlein et al., (1993) Devl. Biol. 160, 51-63; Golembo et al., (1996) supra; Guichard et al., (1999) supra; Pickup and Banerjee, (1999) Dev. Biol. 205, 254-259; Bang and Kintner, (2000) Genes Dev 14, 177-86; Wasserman et al., 2000 supra).

Despite being such important regulators of EGF receptor activation, nothing has been reported about the molecular function of Rhomboid-1 and Star. Although a role in the production or presentation of ligands seems likely, other proposals have included roles in adhesion or promoting active signaling complexes in the plasma membrane (reviewed in Wasserman and Freeman, (1997) Trends in Cell Biol. 7, 431-436).

In the light of evidence for Spitz cleavage (Freeman, (1994) Mech. Dev. 48, 25-33; Schweitzer et al., (1995) Genes Dev. 9, 1518-1529), one model has been that Rhomboid-1 somehow promotes this proteolysis (Golembo et al., 1996 supra), although the lack of recognisable protease domains (Bier et al., 1990 supra) suggests that Rhomboid-1 may not be the protease itself. Indeed, the mammalian homologue of Spitz, TGFα, is proteolytically cleaved by TACE, an ADAM family metalloprotease, which has fly homologues (as yet genetically uncharacterised) and which is unrelated to Rhomboid-1 (Peschon et al., (1998) Science 282, 1281-4). Furthermore, recent evidence has shifted the emphasis towards a role for Star and Rhomboid-1 in ligand presentation at the cell surface (Guichard et al., 1999 supra; Bang and Kintner, 2000 supra; Klämbt, (2000) Curr Biol 10, R388-91). Most directly, Bang and Kintner (2000) have used a *Xenopus* explant assay to conclude that Rhomboid-1 and Star are only indirectly involved in the proteolysis of Spitz, and that their direct role is to alter the conformation and/or presentation of Spitz at the plasma membrane.

The present invention is concerned with the determination of the biological activity of proteins of the Rhomboid family through the study of the mechanism by which Rhomboid-1 and Star control EGF signal activation.

The present inventors have discovered that proteins of the Rhomboid family are a new class of intra-membrane serine proteases, which act on a range of physiological substrates, including EGFR ligands, such as Spitz. The specificity of the proteolytic activity provides indication that molecules which inhibit these proteins may produce specific and highly significant pharmacological effects.

In *Drosophila*, full-length Spitz protein is tightly held in the endoplasmic reticulum (ER) until Star chaperones it to the Golgi apparatus. Contrary to previous assumptions, Rhomboid-1 is shown to be localised in the Golgi apparatus rather than the plasma membrane and directly cleaves Spitz to produce a soluble fragment which binds EGFR.

One aspect of the present invention provides a fragment of a Rhomboid polypeptide wherein the fragment proteolytically cleaves a polypeptide substrate.

A polypeptide substrate may be cleaved within a transmembrane domain.

A fragment of a Rhomboid polypeptide may consist of fewer residues than the full-length Rhomboid polypeptide. For example, a fragment of the Rhomboid-1 polypeptide may consist of less than 355 amino acid residues as described herein.

A suitable substrate may comprise a transmembrane domain which includes a five residue motif which has an equivalent conformation, structure or three dimensional arrangement to that of residues 140-144 of the *Drosophila* Spitz sequence (IASGA) SEQ.ID. 1. More preferably, such a substrate may comprise a seven residue motif which has an equivalent conformation, structure or three dimensional arrangement to that of residues 138-144 of the *Drosophila* Spitz sequence (ASIASGA) SEQ.ID. 2.

Such a polypeptide substrate may comprise a transmembrane domain (TMD) motif which includes one or more of residues 140-144 (IASGA) SEQ.ID. 1, more preferably 138-144 of the *Drosophila* Spitz sequence (ASIASGA) SEQ.ID. 2. Such a TMD motif may preferably include three or more, four or more, five or more, six or more, or all seven such residues. Preferably the TMD comprises at least the GA motif corresponding to residues 143 and 144 of Spitz.

As described above, the substrate is cleaved by the Rhomboid polypeptide within the transmembrane domain.

Other suitable polypeptide substrates may comprise a transmembrane motif which has none of the residues of the *Drosophila* Spitz ASIASGA SEQ.ID. 2 motif, but which instead possess a motif having an equivalent structure which is cleaved by Rhomboid polypeptide (e.g. Gurken, Keren).

For example, a suitable polypeptide substrate may include an amino acid sequence consisting of the transmembrane region of *Drosophila* Spitz polypeptide (residues 139 to 164), Gurken, Keren, or other EGFR ligand exemplified in Table 2 or a variant, allele, derivative, homologue, or mutant thereof.

A variant, allele, derivative, homologue, or mutant may consist of a sequence having greater than about 50% sequence identity with the transmembrane region of the polypeptide, greater than about 60%, greater than about 70%, greater than about 80%, greater than about 90%, or greater than about 95%. The sequence may share greater than about 70% similarity with the sequence of the transmembrane domain of the polypeptide, greater than about 80% similarity, greater than about 90% similarity or greater than about 95% similarity. Preferably, such a variant, allele, derivative, homologue, or mutant comprises residues 141-144 of the *Drosophila* Spitz sequence (IASGA) or residues with an equivalent secondary structure or conformation, more preferably residues 138-144 of the *Drosophila* Spitz sequence (ASIASGA) or residues with an equivalent secondary structure or conformation.

The polypeptide substrate may, for example, be an EGFR ligand, such as Spitz, Gurken, Keren or other EGFR ligand exemplified in Table 2 or a chimeric substrate comprising amino acid residues from two or more EGFR ligands.

Other suitable substrates may be selected from the group consisting of the *S. cerevisiae* polypeptides PET100/YDR079W, OSM1/YJR051W, MGM1/YOR211C, MCR1/YKL150W and CCP1/YKR066C, in particular the group consisting of MGM1/YOR211C and PET100/YDR079W.

A Rhomboid polypeptide fragment consists of fewer amino acid residues than said full-length polypeptide. Such a fragment may consist of at least 255 amino acids, more preferably at least 300 amino acids. Such a fragment may consist of 325 amino acids or less, 300 amino acids or less, or 275 amino acids or less.

Such a fragment preferably comprises residues R152, G215, S217 and H281, more preferably residues W151, R152, N169, G215, S217 and H281, which are important for the catalytic activity of the protein and are highly conserved in the Rhomboid family. A suitable polypeptide fragment may comprise amino acid residues 90 to 328 of the full length *Drosophila* Rhomboid-1 sequence. For example, a polypeptide fragment may comprise residues 90 to 355 of the Rhomboid-1 protein and lack the N terminal cytoplasmic domain of the full length protein or may comprise residues 1 to 328 and lack the C terminal lumenal domain of the full-length protein.

A conserved motif GXSG SEQ.ID. 3 (where X may be any amino acid residue) is frequently found around the active site serine residue (S217), and a Rhomboid polypeptide preferably comprises such a motif, although variants at position 4 exist. In particular, the motif GASG SEQ.ID. 4 may be present.

Amino acid residues of Rhomboid polypeptides are described in the present application with reference to their position in the Rhomboid-1 sequence. It will be appreciated that the equivalent residues in other Rhomboid polypeptides may have a different position and number, because of differences in the amino acid sequence of each polypeptide. These differences may occur, for example, through variations in the length of the N terminal domain. Equivalent residues in Rhomboid polypeptides are easily recognisable by their overall sequence context and by their positions with respect to the Rhomboid TMDs.

A Rhomboid polypeptide may also comprise additional amino acid residues which are heterologous to the Rhomboid sequence. For example, a fragment as described above may be included as part of a fusion protein, e.g. including a binding portion for a different ligand.

A Rhomboid polypeptide suitable for use in accordance with the present invention may be a member of the Rhomboid family or a mutant, homologue, variant, derivative or allele thereof. Suitable polypeptides may have a sequence of *Drosophila* Rhomboid 1, 2, 3 or 4, Human RHBDL-1 (Human Rhomboid-1: Pascall and Brown (1998) FEBS Lett. 429, 337-340), Human RHBDL-2 (NM_017821), Human RHBDL-3 (FIG. 8), Zebrafish RHBDL2 (FIG. 11) *E. coli* glgG, *B. subtilis* ypqP, *P. stuartii* A55862 gene product, *P. aeruginosa* B83259 gene product, *S. cervisiae* YGR101w and *S. cervisiae* YPL246c or other polypeptide as exemplified in Table 1.

Other suitable Rhomboid polypeptides may be found in public domain databases, for example by Blast searching or by an annotation indicating the presence of a rhomboid domain.

A polypeptide which is a member of the Rhomboid family or which is an amino acid sequence variant, allele, derivative or mutant thereof may comprise an amino acid sequence which shares greater than about 18% sequence identity with the sequence of *Drosophila* Rhomboid-1, greater than 25%, greater than about 35%, greater than about 40%, greater than about 45%, greater than about 55%, greater than about 65%, greater than about 70%, greater than about 80%, greater than about 90% or greater than about 95%. The sequence may share greater than about 30% similarity with *Drosophila* Rhomboid-1, greater than about 40% similarity, greater than about 50% similarity, greater than about 60% similarity, greater than about 70% similarity, greater than about 80% similarity or greater than about 90% similarity. Preferably, an amino acid sequence variant, allele, derivative or mutant of a polypeptide of the Rhomboid family retains Rhomboid activity i.e. it proteolytically cleaves a EGFR ligand transmembrane domain substrate.

Sequence similarity and identity is commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4.

Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-

2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a known Rhomboid polypeptide sequence as described herein by insertion, addition, substitution or deletion of 1 amino acid, 2, 3, 4, 5-10, 10-20 20-30, 30-50, or more than 50 amino acids.

Sequence comparison may be made over the full-length of the relevant sequence described herein, or may more preferably be over a contiguous sequence of about or greater than about 20, 25, 30, 33, 40, 50, 67, 133, 167, 200, 233, 267, 300, 333, or more amino acids or nucleotide triplets, compared with the relevant amino acid sequence or nucleotide sequence as the case may be.

A polypeptide which is a member of the Rhomboid family preferably comprises catalytic residues R152, G215, S217 and H281, more preferably catalytic residues W151, R152, N169, G215, S217 and H281. The presence of these conserved residues may be used to identify Rhomboid polypeptides.

Preferably, a Rhomboid polypeptide comprises at least 5 TMDs, with residues N169, S217 and H281 each occurring in different TMD at about the same level in the lipid membrane bilayer. Preferably, a Rhomboid polypeptide also comprises a GxSG SEQ.ID. 3 motif, as described above.

A polypeptide which is a member of the Rhomboid family may also be identified by the presence of a Rhomboid homology domain, as defined by the PFAM protein structure annotation project (Bateman A. et al (2000) The Pfam Protein Families Database Nucl. Acid. Res. 28 263-266). The Pfam rhomboid homology domain is built from a Hidden Markov Model (HMM) using 26 rhomboid sequences as a seed. The Pfam 'rhomboid' domain has the pfam specific accession number PF01694.

Other methods suitable for use in identifying Rhomboid polypeptides are well-known in the art.

Particularly valuable methods include the use of Hidden Markov Models built from groups of previously identified Rhomboid proteins, including, but not limited to *Drosophila* Rhomboids 1-4. Such bio-informatics techniques are well known to those skilled in the art (Eddy S. R. Curr. Opin. Struct. Biol. 1996 6(3) 361-365). Examples of the use of bioinformatics techniques to identify bacterial Rhomboid polypeptides which are then validated by biochemical analysis are provided below.

An EGFR ligand which is a substrate for a Rhomboid polypeptide, is a polypeptide ligand which binds to EGFR. Suitable ligands may include Spitz, Gurken, Keren or other EGFR ligands which are exemplified in Table 2 and homologues, variants, mutants, alleles or derivatives thereof. A EGFR as described herein may, for example, be a *Drosophila* EGFR or a mammalian EGFR.

The present analysis of the mechanism and structure of Rhomboid has led to the discovery of a previously unknown gene (RHBDL3) in the human genome which encodes a Rhomboid polypeptide. This gene occupies 68 kb on chromosome 17 between the annotated genes NJMU-R1 and FLJ11040 (contig NT_010799). The protein sequence of RHBDL3 is shown in FIG. 8 SEQ. ID. 15 and the encoding nucleic acid sequence in FIG. 7 SEQ.ID. 14. The present inventors have also identified and cloned a Zebrafish RHBDL2 gene.

In various aspects, present invention provides an isolated nucleic acid encoding a Rhomboid polypeptide which consists or comprises the amino acid sequence shown in FIG. 8 SEQ.ID. 15 or FIG. 11 SEQ. ID. 17.

The coding sequence may be that shown included in FIG. 7 SEQ.ID. 14 or FIG. 10 SEQ. ID. 16 it may be a mutant, variant, derivative or allele of the sequence shown. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIG. 7 SEQ.ID. 14 or FIG. 10 SEQ.ID. 16 yet encode a polypeptide with the same amino acid sequence.

An isolated nucleic acid may share greater than about 55% sequence identity with the nucleic acid sequence of Human RHBDL3 as shown in FIG. 7 SEQ.ID. 14 or the Zebrafish RHBDL2 sequence shown in FIG. 10 SEQ.ID. 16, greater than 60%, greater than about 70%, greater than about 80%, greater than about 90%, or greater than about 95%. A nucleic acid may share greater than about 65% similarity with Human RHBDL3 or Zebrafish RHBDL2, greater than about 70% similarity, greater than about 80% similarity, greater than about 90% similarity or greater than about 95% similarity.

The present invention also extends to nucleic acid that hybridizes with the sequence shown in FIG. 7 or FIG. 10 under stringent conditions. Suitable conditions include, e.g. for detection of sequences that are about 80-90% identical suitable conditions include hybridisation overnight at 42□C in 0.25M Na$_2$HPO$_4$, pH 7.2, 6.5% SDS, 10% dextran sulfate and a final wash at 55□C in 0.1×SSC, 0.1% SDS. For detection of sequences that are greater than about 90% identical, suitable conditions include hybridization overnight at 65□C in 0.25M Na$_2$HPO$_4$, pH 7.2, 6.5% SDS, 10% dextran sulfate and a final wash at 60□C in 0.1×SSC, 0.1% SDS.

The present invention also includes fragments of such sequences, for example a fragment of the nucleotide sequence of FIG. 7 SEQ.ID. 14 or FIG. 10 SEQ.ID. 16. Suitable fragments may consist of less than 1320 nucleotides, for example from 10, 20, 30, 40 or 50 nucleotides to 1200, 1300, 1305 or 1310 nucleotides. Such a fragment may encode a Rhomboid polypeptide as described herein or may be useful as an oligonucleotide probe or primer. In some embodiments of this aspect of the invention, a fragment of the sequence of FIG. 7 or FIG. 10 does not include the published nucleotide sequence with the accession number BE778475.

Another aspect of the present invention provides an isolated Rhomboid polypeptide encoded by a nucleic acid sequence described above, for example the nucleic acid sequence of FIG. 7 or FIG. 10. Such a Rhomboid polypeptide may comprise or consist of the RHBDL3 amino acid sequence shown in FIG. 8 or the RHBDL2 sequence of FIG. 11.

An isolated Rhomboid polypeptide may share greater than about 70% sequence identity with the amino acid sequence of Human RHBDL3 shown in FIG. 8 or the Zebrafish RHBDL2 sequence of FIG. 11, greater than 80%, greater than about 90%, greater than or greater than about 95%. A Rhomboid polypeptide may share greater than about 70% similarity with Human RHBDL3 or Zebrafish RHBDL2, greater than about 80% similarity, greater than about 90% similarity, or greater than about 95% similarity.

Sequence similarity and identity are discussed elsewhere herein.

The KDEL ER retention signal is not found in natural Rhomboid polypeptides and directs the expressed Rhomboid polypeptide to be retained the ER (endoplasmic reticulum) rather than the Golgi apparatus. As described below, Rhomboid polypeptides labelled with an ER retention signal such as KDEL SEQ.ID. 5 are particularly useful in assay methods of the present invention, as proteolyic cleavage by such polypeptides is independent of the trafficking activity of the Star polypeptide. This overcomes potential problems with variations in secretion efficiency.

Another aspect of the present invention thus provides an isolated Rhomboid polypeptide as described above comprising an N terminal ER retention signal sequence. A suitable signal sequence consists of the amino acid sequence KDEL SEQ.ID. 5.

Such a Rhomboid polypeptide may comprise an N terminal signal sequence consisting of the amino acid sequence KDEL SEQ.ID. 5 and a Rhomboid amino acid sequence as described herein, for example a sequence of one of *Drosophila* Rhomboids 1 to 4, RHBDL-1, RHBDL-2, RHBDL-3, *E. coli* glpG, *Providencia stuartii* A55862, *Pseudomonas aeruginosa* B83259 or other member of the Rhomboid family as exemplified in Table 1.

Another aspect of the present invention provides a nucleic acid encoding a Rhomboid polypeptide as described above. Such a nucleic acid may comprise or consist of a nucleotide sequence described herein.

The skilled person can use the techniques described herein and others well known in the art to produce large amounts of polypeptides and peptides, for instance by expression from encoding nucleic acid.

Peptides can also be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Alanine scans are commonly used to find and refine peptide motifs within polypeptides. This involves the systematic replacement of each residue in turn with the amino acid alanine, followed by an assessment of biological activity. This enable the residues responsible for the activity to be determined.

A "derivative" or "variant" of a polypeptide may include a polypeptide modified by varying the amino acid sequence of the protein, e.g. by manipulation of the nucleic acid encoding the protein or by altering the protein itself. Such derivatives of the natural amino acid sequence may involve one or more of insertion, addition, deletion or substitution of one or more amino acids, which may be without fundamentally altering the qualitative nature of the proteolytic activity of the wild type Rhomboid polypeptide.

Functional mimetics of active fragments of the Rhomboid, Star and EGFR ligand polypeptides provided (including alleles, mutants, derivatives and variants) may also be used in methods of the present invention. The term "functional mimetic" means a substance which may not contain an active portion of the relevant amino acid sequence, and probably is not a peptide at all, but which retains, in qualitative terms, a biological activity of natural Rhomboid, Star or EGFR ligand polypeptide. The design and screening of candidate mimetics is described in detail below.

The isolated and/or purified polypeptide or polypeptide fragment may be used in formulation of a composition, which may include at least one additional component, for example a pharmaceutical composition including a pharmaceutically acceptable excipient, vehicle or carrier.

A composition including a polypeptide or polypeptide fragment according to the invention may be used in prophylactic and/or therapeutic treatment as discussed below.

Various aspects of the present invention relate to screening and assay methods and means, and substances identified thereby, for example, assays for substances which inhibit interaction between a Rhomboid polypeptide of the invention and a polypeptide substrate or between a Star polypeptide and a polypeptide substrate. The polypeptide substrate may be an EGFR ligand.

Further assays are for a compound or substance which interacts with or binds a Rhomboid polypeptide and modulates i.e. increases, stimulates, reduces, inhibits or abolishes, its protease activity.

An assay method for identifying a modulator of Rhomboid polypeptide may include bringing into contact a Rhomboid polypeptide as described herein and a test compound, determining binding of the test compound to the Rhomboid polypeptide and determining the protease activity of the Rhomboid polypeptide in the presence and absence of a test compound which binds the Rhomboid polypeptide. Protease activity may be determined by determining the cleavage of a substrate as described below. The Rhomboid polypeptide may be isolated or comprised in a liposome or cell.

A method of screening for and/or obtaining a substance which modulates activity of a Rhomboid polypeptide may include contacting one or more test substances with the Rhomboid polypeptide in a suitable reaction medium, determining the activity of the treated polypeptide and comparing that activity with the activity of the polypeptide in comparable reaction medium untreated with the test substance or substances. The Rhomboid polypeptide may be in the reaction medium in an isolated form or may be comprised in a liposome or cell.

A difference in activity between the treated and untreated polypeptides is indicative of a modulating effect of the relevant test substance or substances, for example, an inhibiting or enhancing effect.

Activity of a Rhomboid polypeptide may be determined by determining the production of proteolytically cleaved substrate. The Rhomboid polypeptide may, for example, act on a membrane-bound substrate to generate a soluble product which is detected.

According to another aspect of the present invention there is provided an assay method for identifying and/or obtaining a modulator of a Rhomboid polypeptide, which method comprises:

(a) bringing into contact an Rhomboid polypeptide and a test compound in the presence of a polypeptide substrate; and
(b) determining proteolytic cleavage of the polypeptide substrate.

A assay method may be carried out under conditions in which the Rhomboid polypeptide normally catalyses proteolytic cleavage of the polypeptide substrate Cleavage of the substrate may be determined in the presence and absence of test compound. A difference in cleavage in the presence of the test compound relative to the absence of test compound may be indicative of the test compound being a modulator of Rhomboid protease activity.

The Rhomboid polypeptide may be a member of the Rhomboid like family or a mutant, variant or allele thereof. Suitable polypeptides may have a sequence of one of *Drosophila* Rhomboid 1, *Drosophila* Rhomboid 2, *Drosophila* Rhomboid 3, *Drosophila* Rhomboid 4, Human RHBDL-1, Human RHBDL-2 and Human RHBDL-3, *E. coli* glgG, *B. subtilis* ypqP, *P. stuartii* A55862 gene product, *P. aeruginosa* B83259 gene product, *S. cervisiae* YGR101w and *S. cervisiae* YPL246c or other member of the Rhomboid family as exemplified in Table 1.

Any polypeptide substrate which is proteolytically cleaved by a Rhomboid polypeptide may be used in an assay method as described herein. Such substrates are readily identified using standard techniques. A suitable polypeptide substrate may comprise a transmembrane domain having a lumenal portion which has the same conformation as Spitz residues 140-144 (IASGA) SEQ.ID. 1, more preferably the same conformation as Spitz residues 138-144 (ASIASGA) SEQ.ID. 2. Such a lumenal portion may comprise or consist of Spitz residues 140-144 (IASGA) SEQ.ID. 1, more preferably Spitz residues 138-144 (ASIASGA) SEQ.ID. 2. The substrate may comprise a Spitz transmembrane region or a variant, allele, derivative, homologue, or mutant thereof as described above. The polypeptide substrate may be an EGFR ligand, such as an EGFR ligand shown in Table 2.

A suitable substrate may comprise a detectable label such as green fluorescent protein (GFP), luciferase or alkaline phosphatase. This allows convenient detection of the soluble cleaved product and is particularly useful in automated assays.

In preferred embodiments, a substrate does not require the presence of Star polypeptide in order to be cleaved by Rhomboid.

EGFR ligands suitable for use in the present assays are well characterised in the art and may have a structure comprising one or more Epidermal Growth Factor (EGF) domains and a single trans-membrane domain (Groenen L. et al Growth Factors 1994 11(4) 235-257).

Preferably, suitable EGFR ligands have greater than 50% homology, greater than 60% homology, greater than 70% homology, greater than 80% homology greater than 90% homology or greater than 95% homology to a vertebrate EGFR ligand as shown in Table 2. EGF domains may also be identified using pfam (Pfam Accession Number for 'EGF-like domain': PF00008) as described above.

Suitable ligands include Spitz, Gurken, Vein, Keren and variants, mutants, alleles or derivatives thereof. Other examples are shown in Table 2.

In some preferred embodiments, the Rhomboid polypeptide is an RHBDL-2 polypeptide and the polypeptide substrate is a Spitz polypeptide.

A chimeric ligand may have improved properties in methods described herein, for example it may be cleaved more efficiently by a Rhomboid polypeptide, have improved secretion properties or be more readily detected.

Another aspect of the present invention provides a chimeric EGFR ligand comprising sequence from two or more EGFR ligands, for example a chimeric ligand may comprise the transmembrane domain of a first EGFR ligand and the intracellular and extracellular domains of a second EGFR ligand.

A suitable first polypeptide is Spitz and a suitable second polypeptide is TGFα. A chimeric substrate may further comprise a detectable label, such as luciferase, GFP or alkaline phosphatase.

A nucleic acid encoding a preferred chimeric ligand comprises nucleotides 1-130 of the TGFα UTR and signal/propeptide sequence (A of the ATG of TGFα is at 35), a GFP label (nucleotides 131-886), and then the remaining TGFα sequence with the inclusion of Spitz 15aa and TMD (bases 1045-1159).

Assay methods or other methods for obtaining or identifying modulators of Rhomboid activity according to the present invention may be in vivo cell-based assays, or in vitro non-cell-based assays.

Methods may be performed in the presence of 10 µM Baltimastat (British Biotech) to inhibit the non-Rhomboid dependent shedding of substrate and thereby decrease background.

In in vitro assays, the rhomboid polypeptide may isolated or contained in a liposome. Such assays may be performed in the absence of Star polypeptide. Liposome based assays may be carried out using methods well-known in the art (Brenner C. et al (2000) Meths in Enzymol. 322 243-252, Peters et al (2000) Biotechniques 28 1214-1219, Puglielli, H. and Hirschberg C. (1999) J. Biol. Chem. 274 35596-35600, Ramjeesingh, M. (1999) Meths in Enzymol. 294 227-246).

Suitable cell types for in vivo assays include mammalian cells such as CHO, HeLa and COS cells.

It is not necessary to use the entire full length proteins for in vitro or in vivo assays of the invention. Polypeptide fragments as described herein which retain the activity of the full length protein may be generated and used in any suitable way known to those of skill in the art. Suitable ways of generating fragments include, but are not limited to, recombinant expression of a fragment from encoding DNA. Such fragments may be generated by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments (e.g. up to about 20 or 30 amino acids) may also be generated using peptide synthesis methods which are well known in the art.

The precise format of the assay of the invention may be varied by those of skill in the art using routine skill and knowledge. For example, interaction between the polypeptides may be studied in vitro by labelling one with a detectable label and bringing it into contact with the other which has been immobilised on a solid support. Suitable detectable labels include $^{35}$S-methionine which may be incorporated into recombinantly produced peptides and polypeptides. Recombinantly produced peptides and polypeptides may also be expressed as a fusion protein containing an epitope which can be labelled with an antibody.

Fusion proteins may be generated that incorporate six histidine residues at either the N-terminus or C-terminus of the recombinant protein. Such a histidine tag may be used for purification of the protein by using commercially available columns which contain a metal ion, either nickel or cobalt (Clontech, Palo Alto, Calif., USA). These tags also serve for detecting the protein using commercially available monoclonal antibodies directed against the six histidine residues (Clontech, Palo Alto, Calif., USA).

Preferably, assays according to the present invention take the form of in vivo assays. In vivo assays may be performed in a cell line such as a yeast strain, insect or mammalian cell line in which the relevant polypeptides or peptides are expressed from one or more vectors introduced into the cell.

In *Drosophila*, Star chaperones the EGFR ligand from the Endoplasmic Reticulum to the Golgi, where it is cleaved by the Rhomboid-1. In some embodiments, a Star polypeptide may be used in an in vivo assay to deliver an EGFR ligand to the Rhomboid polypeptide.

In assay and other methods according to such embodiments, Rhomboid polypeptide may be contacted with the test compound in the presence of a Star polypeptide. In such methods, the Rhomboid polypeptide, Star polypeptide and EGFR ligand may be present in a cell. This may be achieved, for example by expressing the polypeptides from one or more expression vectors which have been introduced into the cell by transformation.

An assay method for identifying and/or obtaining a modulator of Rhomboid protease may therefore include:
(a) bringing into contact an Rhomboid polypeptide and a test compound in the presence of a Star polypeptide and a EGFR ligand polypeptide; and
(b) determining cleavage of the EGFR ligand.

An assay method may be performed under conditions in which the Rhomboid polypeptide normally catalyses proteolytic cleavage of the EGFR ligand polypeptide.

Cleavage may be determined in the presence and absence of test compound. A difference in cleavage in the presence, relative to the absence of test compound is indicative of the compound being a modulator i.e. an enhancer or inhibitor of Rhomboid activity.

A suitable Star polypeptide may include the *Drosophila* Star (Database Acc No;SWP: P42519)or a variant, homologue, mutant, allele or derivative thereof. A variant, allele, derivative, homologue, or mutant of Star may consist of a sequence having greater than about 70% sequence identity with the sequence of *Drosophila* Star, greater than about 80%, greater than about 90%, or greater than about 95%. The sequence may share greater than about 70% similarity with the sequence of *Drosophila* Star, greater than about 80% similarity, greater than about 90% similarity or greater than about 95% similarity.

In other embodiments of the present invention, a Star-independent EGFR ligand may be used in cell-based assays method and/or a Rhomboid polypeptide which is retained in the ER, and the use of Star in such methods is therefore unnecessary.

Nucleic acid encoding Rhomboid polypeptides, polypeptide substrates and/or Star polypeptides as described above may be provided as part of a replicable vector, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as *E. coli*. This is discussed further below.

Combinatorial library technology (Schultz, J S (1996) Biotechnol. Prog. 12:729-743) provides an efficient way of testing a potentially vast number of different substances for ability to modulate activity of a polypeptide. Prior to or as well as being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trial and error depending upon the type of compound used. Typically, from about 0.01 to 100 nM concentrations of putative inhibitor compound may be used, for example from 0.1 to 10 nM. When cell-based assays are employed, the test substance or compound is desirably membrane permeable in order to access the Rhomboid polypeptide.

Test compounds may be natural or synthetic chemical compounds used in drug screening programmes. Extracts of plants which contain several characterised or uncharacterised components may also be used. A further class of putative inhibitor compounds can be derived from the Rhomboid polypeptide and/or a ligand which binds such as the Spitz TMD. Membrane permeable peptide fragments of from 5 to 40 amino acids, for example, from 6 to 10 amino acids may be tested for their ability to disrupt such interaction or activity. Especially preferred peptide fragments comprise residues 141 to 144 (ASGA) of the Spitz protein, residues 140-144 (IASGA) or residues 138-144 (ASIAGA), or the equivalent regions of other EGFR ligands.

The inhibitory properties of a peptide fragment as described above may be increased by the addition of one of the following groups to the C terminal: chloromethyl ketone, aldehyde and boronic acid. These groups are transition state analogues for serine, cysteine and threonine proteases. The N terminus of a peptide fragment may be blocked with carbobenzyl to inhibit aminopeptidases and improve stability (Proteolytic Enzymes 2nd Ed, Edited by R. Beynon and J. Bond Oxford University Press 2001).

The present application describes two compounds, TPCK and 3, 4-DCI, which have been shown to inhibit Rhomboid activity. Although these compounds are broad spectrum serine protease inhibitors, they represent examples of lead compounds for the rational design of specific Rhomboid inhibitors.

Other candidate inhibitor compounds may be based on modelling the 3-dimensional structure of a polypeptide or peptide fragment and using rational drug design to provide potential inhibitor compounds with particular molecular shape, size and charge characteristics.

Another aspect of the present invention provides a modulator, for example an inhibitor of Rhomboid protease activity or composition comprising a said modulator, isolated and/or obtained by a method described herein.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Another aspect of the present invention provides the use of a Rhomboid polypeptide as described herein in a method for obtaining or identifying a modulator, for example an inhibitor, of Rhomboid serine protease activity. Also provided are methods and uses of a Rhomboid polypeptide in the proteolytic cleavage of the transmembrane domain of a polypeptide substrate.

Rhomboids are involved in quorum sensing—the intercellular signaling carried out by bacteria. Rhomboid inhibitors may be useful in blocking this activity. In one human pathogen (*Providencia stuartii*) the AarA gene is required to generate a signal in a quorum sensing event (Rather, P. N. et al (1999). J Bacteriol 181, 7185-7191). The AarA gene encodes a Rhomboid polypeptide (Gallio, M., and Kylsten, P. (2000). Curr Biol 10, R693-694).

It is shown herein that AarA has the same enzymological activity as *Drosophila* Rhomboid, is therefore useful in screened for inhibitors which block quorum sensing. Pathogenic bacteria use quorum sensing to influence when to express their toxic virulence factors (for example and review—Zhu, J. et al (2002). Proc Natl Acad Sci USA 99, 3129-3134; Miller, M. B., and Bassler, B. L. (2001). Annu Rev Microbiol 55, 165-199); preventing this signal using a Rhomboid inhibitor would stop these pathogens from being virulent. As the inhibitor does not kill the cells, the selective pressure for the organism to acquire resistance to it will be reduced.

Methods described herein may further comprise the step of determining the ability of said test compound to inhibit the infectivity or virulence of a microbial pathogen. This may, for example, comprise determining the expression of toxic virulence factors in the presence and absence of test compound.

Modulators, in particular inhibitors of Rhomboid activity may be useful in the treatment of pathogen infection, for example by yeasts and pathogenic bacteria such as *Providencia stuartii*, *E. coli* 0157 and *Pseudomonas aeruginosa*.

Thus, the present invention extends in various aspects not only to a substance identified as a modulator of Rhomboid activity, in accordance with what is disclosed herein, but also a pharmaceutical composition, medicament, drug or other composition comprising such a substance, a method comprising administration of such a composition to a patient, e.g. for treatment (which may include preventative treatment) of a pathogenic infection or a condition associated with aberrant ErbB or EGF receptor activity, such as cancer, coronary atherosclerosis, psoriasis, wound healing, survival of premature infants, peripheral nerve injuries/neuropathies, use of such a substance in manufacture of a composition for administration, e.g. for treatment of a pathogenic infection or a condition associated with aberrant ErbB or EGF receptor activity, such as cancer, coronary atherosclerosis, psoriasis, wound healing, survival of premature infants, peripheral nerve injuries/neuropathies, and a method of making a pharmaceutical composition comprising admixing such a substance with a pharmaceutically acceptable excipient, vehicle or carrier, and optionally other ingredients.

A condition associated with aberrant ErbB or EGF receptor activity as described above may also be associated with aberrant Rhomboid activity.

A substance identified as a modulator of polypeptide or promoter function using an assay described herein may be peptide or non-peptide in nature. Non-peptide "small molecules" are often preferred for many in vivo pharmaceutical uses. Accordingly, a mimetic or mimick of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Whilst TPCK and 3, 4-DCI have been shown to inhibit Rhomboid, these compounds lack specificity and so are liable to produce undesirable side-effects, if used therapeutically. They may however represent "lead" compounds for the development of mimetics with improved specificity.

Mimetic design, synthesis and testing may be used to avoid randomly screening large number of molecules for a target property.

There are several steps commonly taken in the design of a mimetic from a compound such as TPCK, 3, 4-DCI, or Spitz transmembrane fragments, which have a given target property. Firstly, the particular parts of the compound that are critical and/or important in determining the target property are determined. In the case of a peptide, this can be done by systematically varying the amino acid residues in the peptide, e.g. by substituting each residue in turn.

The essential catalytic residues of polypeptides of the Rhomboid family are highly conserved and correspond to residues N169, G215, S217, H281, W151 and R152 of the *Drosophila* Rhomboid-1 sequence. The essential residues required for cleavage by Rhomboid are residues A141, S142, G143 and A144 of the Spitz sequence. Other important residues include residues A138 S139 and I140 of the Spitz sequence.

Residues which constitute the active region of a peptide or polypeptide are known as its "pharmacophore".

The information provided herein regarding the pharmacophore of the Rhomboid family and its substrate allow their structures to be modelled according their physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process. The discovery of the close relationship between the Rhomboid polypeptide family and the much studied serine proteases provides considerable information regarding the Rhomboid active site.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

For example, mimetics which model the three dimensional conformation of the Rhomboid recognition domain of Spitz (residues 140-144: IASGA SEQ.ID. 1, or more preferably residues 138-144: ASIASGA SEQ.ID. 2) may be used to screen for a compound which binds and inhibits a Rhomboid polypeptide. Such mimetics may include peptide chloromethyl ketone analogues of the Rhomboid binding domain of Spitz, for example comprising the IASGA SEQ.ID. 1 or ASIASGA SEQ.ID. 2 sequence.

Mimetics of substances identified as having ability to modulate Rhomboid polypeptide activity using a screening method as disclosed herein are included within the scope of the present invention.

A polypeptide, peptide or substance able to modulate activity of a polypeptide according to the present invention may be provided in a kit, e.g. sealed in a suitable container which protects its contents from the external environment. Such a kit may include instructions for use.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilizers, buffers, antioxidants and/or other additives may be included, as required.

A convenient way of producing a polypeptide for use in assays and methods according to the present invention is to express nucleic acid encoding it, by use of the nucleic acid in an expression system. Accordingly, the present invention also encompasses a method of making a polypeptide (as disclosed), the method including expression from nucleic acid encoding the polypeptide (generally, nucleic acid according to the invention) and testing for Rhomboid protease activity. This may conveniently be achieved by growing a host cell in culture, containing such a vector, under appropriate conditions which cause or allow expression of the polypeptide. Polypeptides may also be expressed in in vitro systems, such as reticulocyte lysate.

Another aspect of the present invention therefore provides a method of producing a Rhomboid polypeptide comprising:
(a) causing expression from nucleic acid which encodes a Rhomboid polypeptide in a suitable expression system to produce the polypeptide recombinantly;
(b) testing the recombinantly produced polypeptide for Rhomboid protease activity.

Suitable nucleic acid sequences include a nucleic acid sequence encoding a member of the Rhomboid-like family or a mutant, variant or allele thereof as described herein.

A polypeptide may be isolated and/or purified (e.g. using an antibody) for instance after production by expression from encoding nucleic acid (for which see below). Thus, a polypeptide may be provided free or substantially free from contaminants with which it is naturally associated (if it is a naturally-occurring polypeptide). A polypeptide may be provided free or substantially free of other polypeptides.

The recombinantly produced polypeptide may be isolated and/or tested for Rhomboid protease activity by determination of the cleavage of a EGFR ligand polypeptide upon incubation of the polypeptide with the EGFR ligand or other polypeptide substrate.

An isolated nucleic acid as described herein, for example a nucleic acid encoding a Rhomboid polypeptide, may be comprised in a vector. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Further aspects of the present invention provide a host cell containing heterologous nucleic acid encoding a Rhomboid polypeptide which has a KDEL SEQ.ID. 5 tag or which is a fragment of a full length Rhomboid sequence and a host cell containing heterologous nucleic acid encoding a Rhomboid polypeptide and an EGFR ligand polypeptide and, optionally, a Star polypeptide.

The nucleic acid may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

The introduction of nucleic acid into a host cell, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, tested for Rhomboid protease activity and subsequently used as desired, e.g. in the formulation of a composition which may include one or more additional components, such as a pharmaceutical composition which includes one or more pharmaceutically acceptable excipients, vehicles or carriers (e.g. see below).

A Rhomboid polypeptide may be co-expressed in a host cell with a substrate polypeptide and the Rhomboid serine protease activity determined by determining cleavage of the substrate polypeptide. Cleavage may be determined by determining the presence or absence of soluble cleavage products which may be secreted into the culture medium.

The principal determinant of cleavability by Rhomboid-1 is the trans-membrane domain of Spitz, in particular the region between residues 138-144 (ASIASGA) SEQ.ID. 2. A polypeptide comprising a homologous domain is therefore a candidate for being a substrate for a Rhomboid polypeptide. Such polypeptides may be identified by screening databases using standard procedures.

A further aspect of the present invention provides a method of obtaining a substrate for a Rhomboid polypeptide comprising,
(a) providing a test polypeptide,
(b) bringing into contact an Rhomboid polypeptide and the test polypeptide under conditions in which the Rhomboid polypeptide normally catalyses proteolytic cleavage of a substrate; and
(c) determining cleavage of the test polypeptide.

The cleavage of the test polypeptide is indicative of the polypeptide being a Rhomboid substrate.

A test polypeptide may comprise residues 141 to 144 of the *Drosophila* Spitz sequence or residues with an equivalent three dimensional conformation, more preferably residues 140 to 144 or 138 to 144, or residues with an equivalent three dimensional conformation.

A suitable test polypeptide may comprise the transmembrane region of Spitz (residues 139-164), Gurken, Keren, or other EGFR ligand exemplified in Table 2 or a variant, allele, derivative, homologue, or mutant of such a region.

A variant, allele, derivative, homologue, or mutant of the Spitz transmembrane region may consist of a sequence having greater than about 50% sequence identity with the sequence of residues 139 to 164 of *Drosophila* Spitz, greater than about 60%, greater than about 70%, greater than about 80%, greater than about 90%, or greater than about 95%. The sequence may share greater than about 70% similarity with the sequence of residues 139 to 164 of *Drosophila* Spitz, greater than about 80% similarity, greater than about 90% similarity or greater than about 95% similarity.

Suitable test polypeptides may be identified by screening databases using the bioinformatics techniques discussed above.

Another aspect of the present invention provides a fragment of a Rhomboid polypeptide which has no proteolytic activity and which, when expressed in a cell, reduces or abolishes the proteolytic activity of an active Rhomboid polypeptide expressed in the same cell. For example, a fragment consisting of residues 1 to 149 of the Rhomboid-1 sequence, the N terminal cytoplasmic domain, first transmembrane region and part of the first lumenal loop possesses this dominant negative activity.

A further aspect of the present invention is a nucleic acid encoding such a Rhomboid polypeptide fragment.

A dominant negative polypeptide fragment may be used to 'knock out' the activity of endogenous Rhomboid polypeptide as described herein. A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may, for example, be a bacteria, archaea, unicellular eukaryote or may be comprised (e.g. in the soma) within an organism which is a fungi, plant or animal, including vertebrates and invertebrates and in particular a mammal, which may be human or non-human, such as rabbit, guinea pig, rat, mouse, rat or other rodent, cat, dog, pig, sheep, goat, cattle or horse, or which is a bird, such as a chicken.

Genetically modified or transgenic organisms comprising such a cell are also provided as further aspects of the present invention. Such animals may be useful in the study of diseases associated with Rhomboid dysfunction.

Another aspect of the present invention provides the use of a dominant negative Rhomboid polypeptide fragment as described herein in an in vitro method of inactivating a Rhomboid polypeptide in a cell comprising expressing said polypeptide in said cell.

Aspects of the present invention will now be illustrated with reference to the accompanying figures described below and experimental exemplification, by way of example and not limitation. Further aspects and embodiments will be apparent to those of ordinary skill in the art. All documents mentioned in this specification are hereby incorporated herein by reference.

FIG. 1 shows a series of GFP-tagged derivatives of the Spitz/TGFα chimeras and Spitz deletions expressed in COS cells and localised using immunofluorescence.

FIG. 2 shows a model of the mechanism of Star and Rhomboid-1 as described in the present application. Spitz is retained in the ER (a) until Star promotes its relocalisation (b) to the Golgi apparatus. There it encounters Rhomboid-1, which induces its cleavage (c), releasing a soluble lumenal fragment. This is then secreted from the cell (d), so that it can activate the EGF receptor.

FIG. 3 shows a summary of interactions between Spitz, Star and Rhomboid-1. The chaperoning function of Star is mediated primarily through the lumenal domains of Star and Spitz, although the cytoplasmic domains contribute to a lesser extent (indicated by arrow). Spitz is otherwise retained in the ER via its cytoplasmic domain. In the Golgi apparatus, the TMD region of Rhomboid-1 induces the cleavage of Spitz within the Spitz TMD.

FIG. 4 shows the N and C series of Rhomboid-1 truncations. The N series were triple HA-tagged at the N-terminus and truncated as marked by the arrowheads above the line; the C series were triple HA-tagged at the C-terminus and truncated as marked by the arrowheads below the line. Precise coordinates are shown in Table 3.

FIG. 5 shows an alignment of the three closest human rhomboid homologues with *Drosophila* rhomboid-1 SEQ.ID. 13: RHBDL-1 SEQ.ID. 11 (also known as RHBDL), RHBDL-2 SEQ.ID. 12 and RHBDL-3 SEQ.ID. 15. In particular the amino acid sequence of RHBDL-3 SEQ.ID. 15 is shown.

The boundary between the cDNA sequence and predicted sequence of RHBDL3 is indicated. The conserved serine protease motif (GASGG) SEQ.ID. 6 surrounding the active serine is shown above the sequences; the other catalytic residues we have identified are indicated by arrowheads. Identical residues are shaded black; conservative changes are shaded grey. This alignment was generated with the GCG program 'pileup'.

FIG. 6 shows a schematic of Spitz/TGFα chimeras, indicating which retained the ability to be cleaved by Rhomboid-1. Numbered coordinates within the TMDs represent the TMD residues of Spitz that have been replaced by corresponding TGFα residues. The recognition domain for Rhomboid-1 cleavage maps to the lumenal quarter of the TMD, i.e. Spitz residues 140-145.

FIG. 7 shows the nucleic acid coding sequence of RHBDL3 SEQ.ID. 14. The sequence is predicted by Genemark (and supported by a partial EST [accession number BE778475] indicated by the horizontal line below the sequence).

Untranslated regions are not shown; the sequence begins with the ATG codon predicted to encode the first methionine. Arrows represent positions of introns. Alternating upper/lower case is used to distinguish adjacent exons. This ORF spans 55152 nucleotides of genomic sequence on human chromosome 17 (from contig accession number NT_010799).

FIG. 8 shows the amino acid sequence of RHBDL3 SEQ.ID. 15.

FIG. 10 shows the nucleotide sequence of the Zebrafish RHBDL2 SEQ.ID. 11.

FIG. 11 shows the amino acid sequence of the Zebrafish RHBDL2 SEQ.ID. 17.

Figure 1:
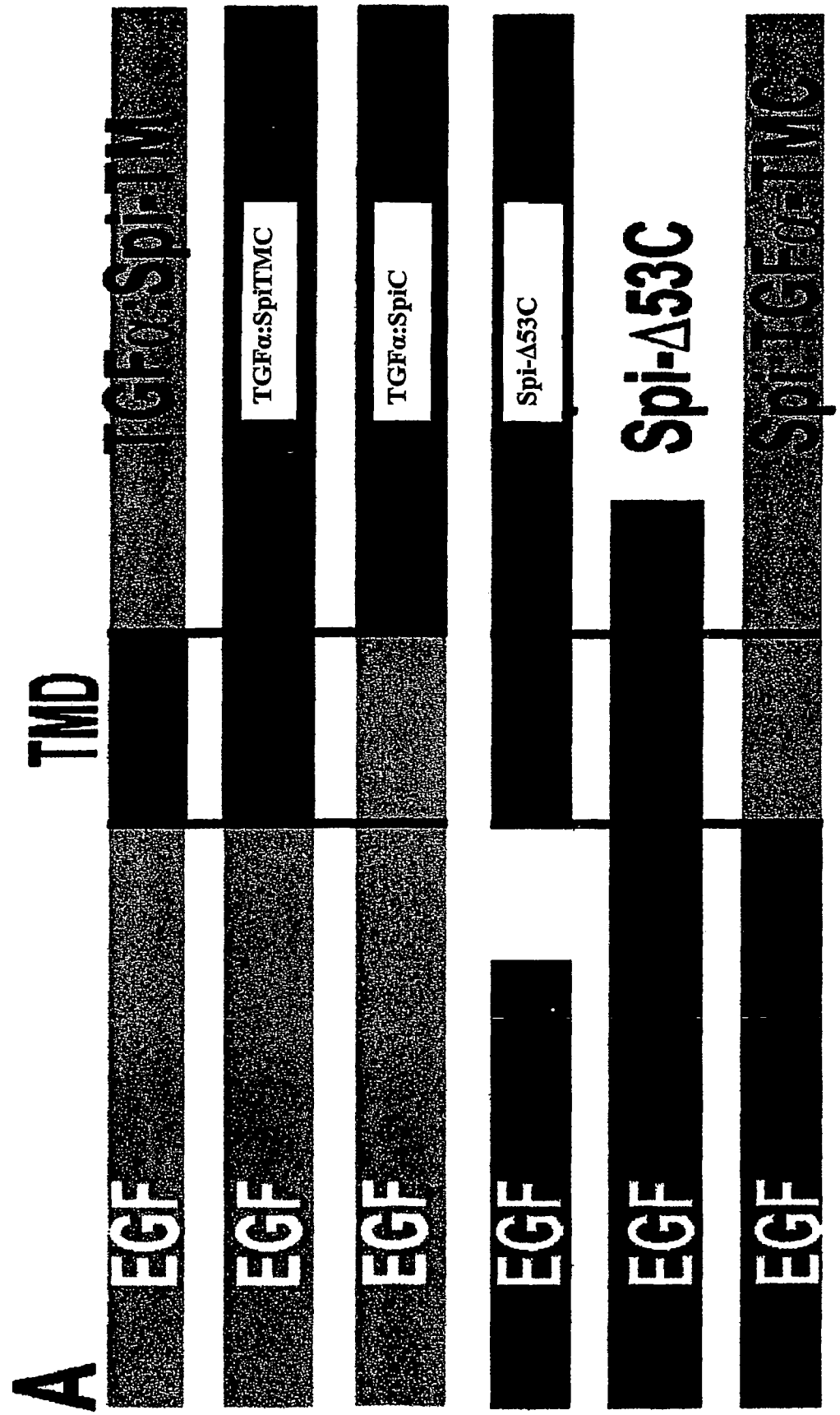
Figure 2:
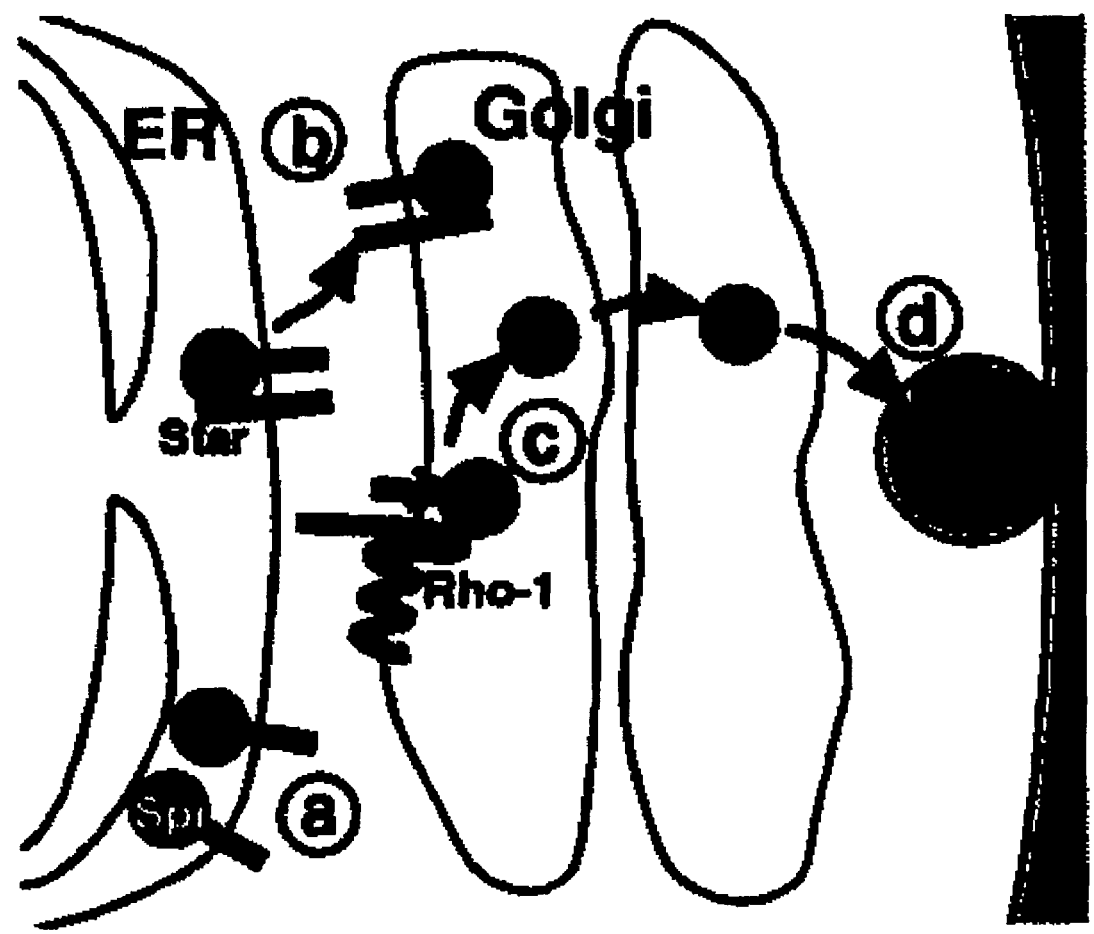
Figure 3:
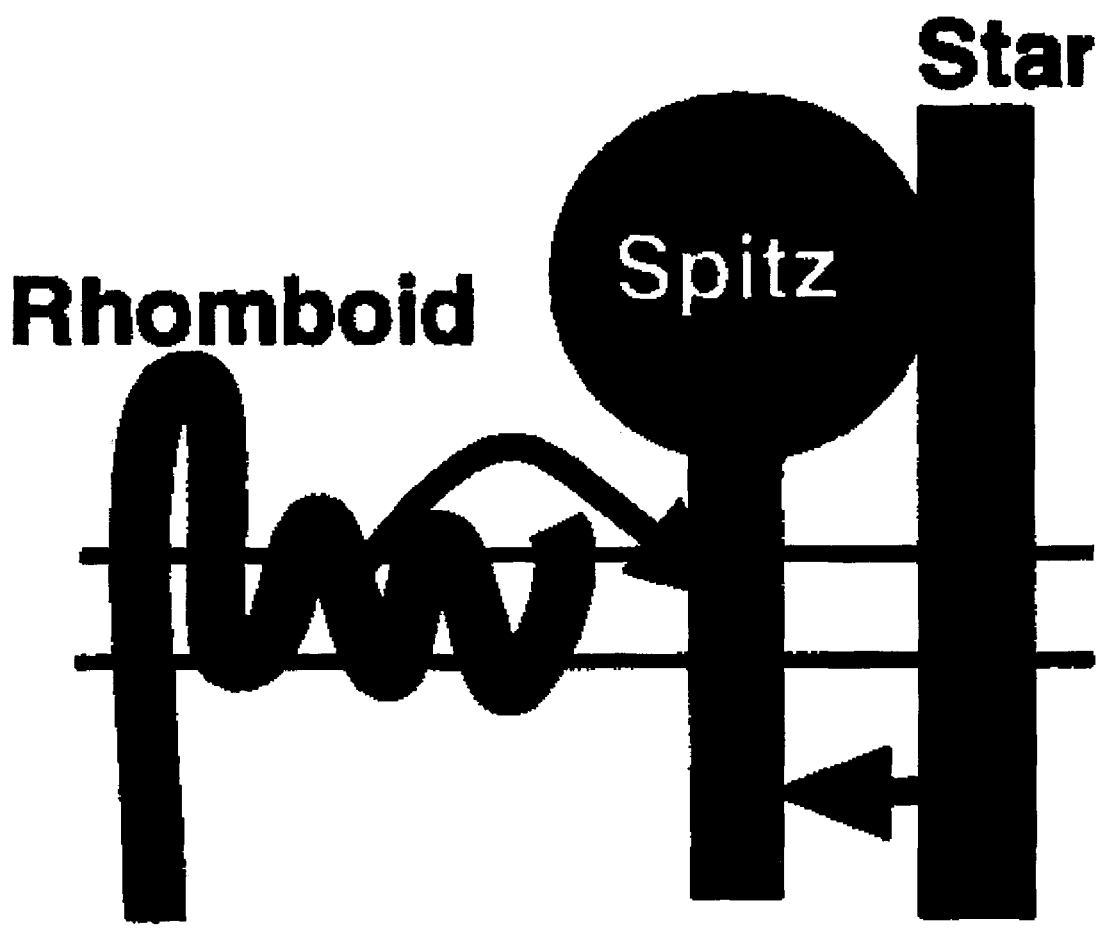

Table 1 shows a non-exhaustive list of database sequences of Rhomboid polypeptides.

Table 2 shows a non-exhaustive list of database sequences of EGFR ligands.

Table 3 shows the Rhomboid deletion mutants used in the experiments described below.

Experimental

Materials and Methods

*Drosophila* Stocks

The following fly lines were generated by standard techniques: UAS-mycSpi, UAS-Rho-1HA, UAS-Rho-1N, and UAS-Rho-1. Other lines used included MS1096-Gal4 (Capdevila, J. and Guerrero, I. (1994). EMBO J. 13, 4459-4468.), hsp70-rho-1 (Freeman, M. et al (1992). Development 116, 335-346) and a salivary gland specific Gal4 line (1824 in the Bloomington Stock Centre). All other stocks are listed in Flybase.

DsRNA Interference

RNAi was performed by a modification of the protocol of Kennerdell, J. R. and Carthew, R. W. (Kennerdell, J. R. and Carthew, R. W. (1998). Cell 95, 1017-26).

100 μg of RNA corresponding to each gene of interest was synthesized by in vitro transcription from 5 μg linearized plasmid templates according to manufacturer's instructions (Promega Ribomax system). The resulting RNA was purified using the RNeasy protocol (Qiagen), denatured by boiling, and annealed in 1 mM Tris-HCl pH7.4, 1 mM EDTA overnight. The resulting dsRNA was ethanol precipitated and resuspended in injection buffer (0.1×PBS) at a concentration of 1-2 mg/ml as estimated by agarose gel electrophoresis. Embryos were collected over a 1 hour interval from 2-7 day old cages of y w adult flies, placed onto glass slides, dehydrated for 5 minutes, and microinjected laterally through their chorions under Voltalef's 10S oil. Following a 48 hour incubation in a humidified chamber at room temperature, the lethality and the cuticle phenotype were assessed by standard methods.

Construct

Spitz was tagged with a single myc tag between residues 123 and 124 and cloned into the pUAST vector for fly transformation. The EGFP ORF (Clontech) was inserted into a BsiWI site between residues 33 and 34 of Spitz. A BsiWI site was introduced by PCR mutagenesis into the N-termini of TGFα and the chimeras containing the TGFα N-terminal domain, allowing the EGFP ORF to be inserted between residues 32 and 33. The Spitz/TGFα chimeras, SpiΔ53C, Spi-15aa and sspitz, tagged with EGFP ORF in the same position as Spitz, are described elsewhere (Bang and Kintner, 2000 supra, Schweitzer, R. et al (1995). Genes Dev. 9, 1518-1529.). Spi:TGFα-C includes residues 1-167 of Spitz and 128-160 of human TGFα; it was also EGFP tagged between residues 33 and 34. Rhomboid-1 was tagged at its N-terminus with a triple HA tag and cloned into the pUAST and pcDNA3.1 vectors. A triple myc tag was inserted between residues 3 and 4 of Star or, in a second construct, between residues 83 and 84.

Rho-1N and Rho-1ΔN include residues 1-89 and 89-355, respectively (the first TMD starts at residue 101).The precise coordinates of the Rhomboid-1 N and C terminal truncation series are shown in Table 3. StarΔ291C, Δ266C and Δ47C were made by inserting stop codons at residues 310, 331 and 551, respectively. Unless otherwise noted, all constructs for tissue culture were inserted into pcDNA3.1 (Invitrogen) except Spi-15aa and spi:TGFα-TMC which were in pCS2 (Bang and Kintner, 2000 supra).

Spitz Cleavage in Embryos

Embryos were collected over 24 hours from cages with 500-1500 w; arm-gal4 UAS-mycSpi females crossed to 100-300 w; hs-rho1; UAS-S males. The resulting embryos were heat shocked at 37° C. for 1.5 hours to induce the expression of rhomboid-1, and allowed to recover at 25° C. for 0-2 hours. The embryos were then dechorionated and lysed in 1 ml ice cold RIPA buffer containing a protease inhibitor cocktail (Roche). Insoluble material was removed by centrifugation, and mycSpitz was immunoprecipitated overnight at 4° C. with 20 μl anti-Myc antibody (9E10, Santa Cruz) directly coupled to agarose beads. The beads were stringently washed in RIPA buffer, resuspended in 20 μl SDS sample buffer, and boiled for 5 minutes. MycSpitz was detected by western blot with 1:1000 rabbit anti-myc (A14, Santa Cruz).

Glycosylation Analysis in Embryos

Embryos were collected as described above and extracts were treated with a variety of deglycosylating enzymes. Endoglycosidase $H_f$ (Endo-H) removes high-mannose N-linked glycans that are the hallmark of ER-resident proteins; peptide-N-glycosidase F (PNGase F) removes both high mannose glycans and also complex N-linked glycans, typical of Golgi modification; O-glycosidase removes many O-glycans, which are added only in the Golgi; finally, neuraminidase is an exoglycosidase of broad specificity which can improve the efficiency of O-glycosidase. All enzymes were used on denatured samples according to the manufacturers' instructions.

Cell Culture

COS cells were grown in DMEM medium (supplemented with 10% foetal calf serum), and transfected with FuGENE 6 Transfection Reagent (Roche). Cells were transfected in 35 mm culture wells with 25-250 ng of each construct and empty plasmid to bring the total DNA to 1 μg per well. 24-30 hours post-transfection the medium was replaced with serum-free medium; this was harvested 24 hours later and cells were lysed in SDS-sample buffer. GFP was detected in conditioned medium and cell lysates by western blot with a rabbit polyclonal antibody. For some experiments the serum-free medium was supplemented with the metalloprotease inhibitor batimastat (British Biotech) or ilomostat (Calbiochem).

Yeast Strains

YGR101w and YPL246c were C-terminally GFP tagged in the genome directly by PCR (Wigge, P. A. et al (1998). J Cell Biol 141, 967-977.) in the diploid strain K842 (Nasmyth et al. (1990) Cell 62, 631-647.). Live cells were imaged on a Radiance Confocal Microscope (BioRAD).

Immunohistochemistry

Cells seeded and transfected on cover slips were fixed for 20 minutes in 4% paraformaldehyde in PBS, and permeabilised for 10 minutes in 0.1% TritonX-100 in PBS. Cells were blocked overnight with 1% BSA, and subsequently incubated at room temperature with primary and secondary antibody for 1.5 h and 1 h, respectively. GFP fluorescence was often greatly reduced after fixation and required staining with anti-GFP (1:5000) for visualisation. The following primary antibodies were used: mouse anti-Myc 9E10 (Santa Cruz Biotechnology) at 1:250, rat anti-HA (Roche) at 1:500, rabbit anti-PDI (Calbiochem) at 1:250, rabbit anti-Giantin (Seelig et al., (1994) J. Autoimmun. 7, 67-91) at 1:500, mouse anti-p115 (Transduction Labs; a second mammalian cell Golgi marker) at 1:250. Alexa Fluor 568 (red) and Alexa Fluor 488 (green)-conjugated secondary antibodies from Molecular Probes were used at 1:500. Salivary glands were stained according to Munro and Freeman (2000) using 1:400 mouse anti-*Drosophila* Golgi (Calbiochem) and 1:400 rabbit anti-HA (Y11, Santa Cruz). All fluorescent images were collected on an MRC Radiance confocal microscope (Biorad).

Protease Inhibitor Assay

Cells were transfected as standard with 1 ng of Rhomboid-1 DNA (in 1 μg total DNA) and were then incubated in serum-free medium for 24 hours. The medium was then replaced with 0.5 ml serum free medium containing protease inhibitor at the indicated concentration and incubated for 1 hour. After 1 hour, the medium was collected, cleared by centrifugation, dialysed overnight against several changes of water and lyophilised. The resulting pellets were re-suspended in SDS sample buffer, boiled and analysed by Western blot. Transfections with a secreted form of Spitz were used in parallel to control for non-specific toxicity of the protease inhibitors or general inhibition of the secretory pathway.

Assay for Inhibitors of Human Rhomboid (RHBDL2)

HeLa cells are co-transfected with;
(a) RHBDL2 construct ("HAn RHBDL") comprising the RHBDL2 coding sequence with a triple N-terminal HA tag, inserted into the vector pcDNA 3.1+ (Invitrogen), and;
(b) Substrate construct containing the preferred/optimized substrate ("GFP-TGF-Spi-TGF") inserted into pcDNA 3.1+ (Invitrogen).

A control vector containing TGF-alpha with an N-terminal GFP tag (with or without a C-terminal HA tag) may be used as a positive control for protein secretion into the medium and is independently transfected into the HeLa cells.

Transfection of construct (b) into HeLa cells in the absence of construct(a) acts as a control for endogenous cleavage of the substrate. Optionally, a metalloprotease inhibitor such as batimastat may be used to minimize endogenous substrate cleavage in the HTS assay.

Transfected cells are then incubated with test compounds e.g. in a 96-well microplate format.

Supernatants are then collected from the wells and assayed for the presence of GFP in the medium using conventional techniques.

For example, GFP may be captured with a polyclonal or monoclonal antibody, washed and then the captured GFP detected with a polyclonal or monoclonal antibody conjugated to an enzyme (capture ELISA) or with a fluorescent label.

For ELISA, a suitable polyclonal anti-GFP conjugated to horseradish peroxidase or to alkaline phosphatase is commercially available. Such a conjugate is preferred since the number of incubations required is reduced. Alternatively a biotinylated anti-GFP antibody in combination with an avidin or strepavdin enzyme conjugate could be used.

For a fluorescence assay, Europium- or Terbium-labelled antibody or streptavidin are suitable (e.g. Delphia or Lance reagents, Perkin Elmer). These are labels with a long fluorescence lifetime and can improve the signal:noise ratio.

A variation of the above is to replace GFP in the GFP-TGF-Spi-TGF construct (or to add to the construct) with an enzyme label at the N-terminus to give a direct assay for the cleaved substrate in the medium. Suitable enzymes include Renilla luciferase (Lui, J., and Escher, A. (1999) Gene 237, 153-159) and secretable alkaline phosphatase sequence (SEAP)(Clontech).

Cloning Bacterial Rhomboids

Bacterial Rhomboid genes were cloned by PCR from genomic DNA and inserted into pcDNA3.1 (Invitrogen). Activities were assayed by the standard COS cell assay described above, although typically 100 ng of rhomboid DNA was transfected into a 35 mm dish of COS cells.

Yeast Knockouts

Knockouts of *Saccharomyces cerevisiae* rhomboid genes were done by standard procedures (Rothstein R J. 1983. Methods Enzymol 101, 202-11). Rescue experiments were performed by cloning wild-type or mutated forms of rhomboids into a 2-micron plasmid, which is maintained as a single copy in yeast cells. The plasmid was transformed into the relevant rhomboid knockout cells and its ability to rescue the specific knockout phenotype was assessed.

Zebrafish Knockouts

Knockout of the zebrafish RHBDL2 was performed by standard procedures (McClintock J M, Kheirbek M A, Prince V E. 2002. Development. 129, 2339-2354.). A morpholino antisense oligonucleotide (TCTTGCTCTTCGGTGTCAT-TATCGC) SEQ.ID. 7 complementary to the region of the cDNA surrounding the start of translation was injected into 1-4 cell embryos at 2-4 μM. After 24 and 48 hours the phenotype was assessed and compared with wild-type embryos of equivalent stages. In situ hybridisation to RHBDL2 was performed by standard techniques.

Results

Spitz is Cleaved by a Rhomboid and Star Dependent Mechanism

*Drosophila* embryos were investigated for the cleavage of Spitz in response to Rhomboid and Star. UAS-driven Spitz which was myc-tagged near its N-terminus, was ubiquitously expressed in embryos under the control of armadillo-Ga14, in the presence or absence of ubiquitous Star and/or heatshock inducible Rhomboid-1; tagged Spitz was then immunoprecipitated from embryo extracts (Note that these embryos contain endogenous Star and Rhomboid as well as the ectopically expressed transgenes).

No cleavage of Spitz was induced by Rhomboid-1 alone. Very low level of cleavage was detected in the presence of Star alone, although a new, more slowly migrating species of Spitz appeared, along with a small amount of low molecular weight product.

In embryos expressing Spitz with Star and inducible Rhomboid-1, a truncated form of Spitz appeared in response to the induction of Rhomboid-1 expression. This is the first direct evidence for the cleavage of Spitz in flies, and it demonstrates that proteolysis occurs in response to Rhomboid expression.

This biochemical assay of Spitz activation correlates well with previous genetic evidence showing that Star and Rhomboid are both required for EGF receptor activation and that they act synergistically.

A time course indicated that cleaved Spitz is unstable, declining substantially by 60 minutes after heatshock. Endocytosis participates in this instability, since cleaved Spitz accumulated to higher levels when endocytosis was blocked in a shibire$^{ts}$ mutant background in which *Drosophila* dynamin is inactivated (van der Bliek and Meyerowitz (1991) Nature 351, 411-4.).

This result also indicates that endocytosis is not required for the Rhomboid-1 and Star-induced cleavage of Spitz.

Spitz Cleavage in Mammalian Cells

The proteolytic cleavage assay was recapitulated in a mammalian tissue culture system. Spitz was tagged with GFP near its N-terminus and transiently expressed in COS cells, in the presence or absence of Star and/or Rhomboid-1. The accumulation of the soluble extracellular fragment of GFP-Spitz in the cell medium was then measured by western blot.

Very similar results to those in embryos were obtained: no cleaved Spitz was detected in the absence of Star and Rhomboid-1, nor in the presence of Rhomboid-1 alone. Star induced a low level of cleaved Spitz as well as a new, higher molecular weight full-length Spitz band in the cell lysates. The co-expression of Spitz with Star and Rhomboid-1 led to the efficient cleavage of membrane bound Spitz into a soluble form. Again, Star and Rhomboid-1 were both required for efficient cleavage and they acted synergistically. The size of the released GFP-Spitz fragment was indistinguishable from that of an artificially secreted form of GFP-Spitz, in which the protein was truncated between the EGF domain and the TMD.

The Rhomboid-1 and Star-dependent cleavage of Spitz was not COS cell-specific. Identical cleavage was induced in a broad range of mammalian cell lines, including HeLa, NIH3T3 and CHO.

All cells were tested using the same assay as COS cells i.e. co-transfect Rhomboid, Star and substrate and test medium and lysate for cleaved substrate.

Mammalian cells were also found to be sensitive to overexpression of Rhomboid-1: at the highest levels, Spitz secretion is compromised due to fragmentation of the golgi apparatus when high levels of Rhomboid are expressed.

Spitz is Not Cleaved by a TACE-like Metallo-proteases

Spitz, Star and Rhomboid-1 are the only *Drosophila* proteins present in the transfected mammalian cells. A possible hypothesis is that these proteins are able to recruit a mammalian protease to a processing complex. If this were the case, the principle candidate for the putative mammalian protease would be a member of the ADAM family of metalloproteases. These proteases have broad specificity and are responsible for the release of a large number of mammalian growth factors, including the Spitz homolog, TGFα. The possible involvement of these proteases was tested with the potent metalloprotease inhibitor batimastat (British Biotechnology) at 1 μM and 10 μM. As expected, batimastat inhibited the release of TGFα at 10:M concentrations in this assay, but it did not affect the cleavage of Spitz by Rhomboid and Star.

The same result was obtained with ilomostat (Calbiochem), another broad spectrum metalloprotease inhibitor. Rhomboid-induced Spitz cleavage is therefore not dependent on a metalloprotease. Interestingly, the lower-level secretion of Spitz induced by Star alone is completely inhibited by 1:M batimastat, implying that this occurs by a mechanism distinct from the Rhomboid-induced cleavage.

Star and Rhomboid-1 are therefore sufficient in themselves to catalyse the cleavage of Spitz.

RNA interference was used to inactivate the *Drosophila* homologue of TACE (CG7908), the specific metalloprotease required for TGFα cleavage (for which no mutant yet exists in *Drosophila*). If TACE were necessary for Spitz cleavage, blocking its expression by RNAi should cause a spitz-like phenotype. In fact, the embryos thus injected were indistinguishable from wild-type, providing further indication that *Drosophila* TACE is not an essential component of Spitz activation.

Intracellular Localisation of Spitz, Star and Rhomboid

COS cells expressing combinations of Spitz, Star and Rhomboid-1 were examined to discover the localisation of the proteins. As well as GFP-Spitz, HA-tagged Rhomboid-1 and myc-tagged Star, which were functional in the cleavage assay, were used. Spitz was located only in the endoplasmic reticulum (ER), as demonstrated by its characteristic perinuclear and reticular staining, and by its co-localisation with the ER marker protein disulphide isomerase (PDI). Star had a more complex pattern; it was in the ER, as determined by its co-localisation with PDI. In 80-90% of cells, Star was also in the Golgi apparatus and, in about half of these cells, in the plasma membrane as well. Our finding that Star was present in the ER is consistent with its reported localisation in the *Drosophila* oocyte (Pickup and Banerjee, 1999 supra). Rhomboid-1 was in the Golgi apparatus, as determined by its co-localisation with the Golgi protein giantin (Seelig et al., 1994 supra); importantly, no Rhomboid-1 could be detected in the ER. Expression of high levels of Rhomboid-1 caused the Golgi apparatus to fragment; in these cells, Rhomboid-1 still co-localised with giantin in the Golgi fragments, but was also seen at the plasma membrane in about 10% of cells. This Golgi fragmentation is a probable explanation for our observation that high levels of Rhomboid reduced Spitz secretion.

Star Relocalises Spitz Within the Cell

Co-expression of Spitz and Star caused a striking relocalisation of Spitz: instead of being in the ER, Spitz was now located in the Golgi apparatus and the plasma membrane.

When in the Golgi apparatus, Spitz always co-localised with Star, but this co-localisation became less uniform later in the secretory pathway. In some cells, Spitz and Star remained together in the plasma membrane; in others, Spitz was in the plasma membrane whereas Star was confined to the ER and Golgi. These staining patterns suggest that Star and Spitz need to associate for Spitz to move from the ER into the Golgi, but that the subsequent translocation of Spitz through the secretory pathway is not dependent on Star, although the two proteins do sometimes remain co-localised.

The co-expression of Spitz and Rhomboid-1 had no effect on the localisation of either protein: Spitz remained in the ER and Rhomboid in the Golgi apparatus. When Spitz, Star and Rhomboid-1 were co-expressed, Spitz was seen in the Golgi apparatus, providing indication that cleavage and/or subsequent secretion are rate-limiting, not the translocation of Spitz from the ER to the Golgi.

These results indicate that Star regulates EGF receptor signaling by moving Spitz, which is normally retained in the ER, into the Golgi apparatus where it encounters the proteolytic action promoted by Rhomboid-1. In the situation where Spitz and Star are co-expressed in the absence of Rhomboid-1, the uncleaved form of Spitz moves through the Golgi to the plasma membrane. But when the three proteins are co-expressed, Spitz is efficiently cleaved and secreted and therefore does not reach the plasma membrane.

Localisation in *Drosophila* and Yeast Cells

HA-tagged Rhomboid was expressed under the control of the Gal4/UAS system in larval salivary glands, which have much larger cells than most in *Drosophila* and are therefore well-suited for sub-cellular localisation of proteins. All detectable HA-Rhomboid was located in punctate Golgi-like structures in these cells and it co-localised precisely with a known Golgi marker. This indicates that Rhomboid-1 is indeed localised in the Golgi apparatus in *Drosophila*, and that it does not normally reside in the plasma membrane. This localisation is evolutionarily conserved, as tagged versions of the *Saccharomyces cerevisiae* Rhomboid homologue YPL246c was also localised in intracellular Golgi-like compartments and were not associated with the plasma membrane. The *Saccharomyces cerevisiae* Rhomboid homologue YGR101w was found to be localised in the mitochondria.

A biochemical approach was used to analyse the location of Spitz in *Drosophila* cells, and to determine whether it is relocalised by Star. Spitz protein migrated at a higher molecular weight than expected on western blots, and the bands had a diffuse appearance. This provides indication that, as predicted, and like TGFα (Teixido et al., (1990) J Biol Chem 265, 6410-5.; Rutledge et al., (1992) Genes Dev. 6, 1503-1517; Schweitzer et al., 1995 supra), the extracellular portion of the molecule is glycosylated.

This was confirmed with a variety of deglycosylation enzymes, and the specificity of these enzymes allowed us to infer the sub-cellular localisation of Spitz. Endo-H removed all evidence of glycosylation from the form of full-length Spitz that occurs in the absence of Star. As Endo-H is an enzyme that removes only simple, high-mannose N-linked glycosylation characteristic of ER modification, this indicates that this form of Spitz is resident only in the ER.

As previously noted, when Spitz was co-expressed with Star, a band of increased molecular weight appeared; Endo-H could not deglycosylate this form of Spitz. Instead, it was sensitive to enzymes that remove O-linked sugars that are added only in the Golgi apparatus (O-glycosidase and neuraminidase). The cleaved form of Spitz had the same pattern of sensitivity as the Star-dependent form. These results show that in *Drosophila* embryos, Spitz is located solely in the ER until Star exports it to the Golgi apparatus, where it acquires O-glycosylation. Rhomboid did not affect the glycosylation of Spitz: in embryos, as in mammalian cells, its only function seems to be to promote cleavage.

Essential Domains of Spitz

A series of GFP-tagged chimeras between Spitz and human TGFα and deletions based on those of Bang and Kintner (Bang and Kintner (2000)supra) were examined in the COS assay (FIG. 1). TGFα was constitutively secreted from COS cells efficiently by a mechanism that was sensitive to metalloprotease inhibitors; the addition of Star and/or Rhomboid had no detectable effect either on its secretion or its localisation throughout the secretory pathway and at the plasma membrane.

Requirement for Star-dependent Relocalisation

The replacement of the TGFα TMD with that from Spitz did not affect its broad distribution. In contrast, TGFα chimeras containing the Spitz cytoplasmic domain were retained tightly in the ER, implying that this domain contains the information necessary for Spitz ER retention. Deletion, however, of the 53 C-terminal amino acids of Spitz (leaving only the 13 membrane-proximal amino acids of the cytoplasmic domain) did not compromise ER retention.

The property of being relocalised by Star did not map to a single domain of Spitz. Deletion of the 15 residues between the EGF domain and the TMD reduced the efficiency of relocalisation substantially: some was relocalised to the Golgi apparatus by Star but much remained in the ER; the poor relocalisation of Spi-Δ15 was confirmed by the absence of a shifted, O-glycosylated full-length band in the cell lysates. In contrast, removal of only the 8 juxtamembrane residues did not reduce Star-dependent relocalisation. Removal of the cytoplasmic C-terminal 53 residues also made Star relocalisation less efficient than wild-type—again, some Spitz was retained in the ER; in this case a weak O-glycosylated band is visible in cell lysates, indicating that more of Spi-Δ53C than Spi-Δ15 gets to the Golgi.

Together, these results show that both the lumenal and cytoplasmic domains of Spitz are involved in relocalisation.

However, another chimera demonstrated that the lumenal domain of Spitz is sufficient for Star-dependent relocalisation. Thus, a construct which comprises the extracellular domain of Spitz linked to the TMD and cytoplasmic domain of TGFα had a distribution indistinguishable from TGFα (ER, Golgi, some plasma membrane) but upon co-expression of Star, it was no longer detectable in the ER and the cell surface staining became more prominent. Therefore, despite the absence of the Spitz ER retention signal, this chimera was re-localised by Star. In contrast, TGFα chimeras containing the Spitz cytoplasmic domain were not re-localised by Star, indicating that this domain is not sufficient for Star re-localisation.

Requirement for Rhomboid-dependent Cleavage

Strikingly, the replacement of the TGFαTMD (trans-membrane domain) with the Spitz-TMD was sufficient to render the chimera (TGFα:SpiTM) sensitive to Rhomboid-1-promoted cleavage, albeit with variable efficiency. This cleavage was apparent in the cell lysates as new Rhomboid-1-dependent bands; it was not detectable in the medium, although this may be due to poor secretion of the cleaved product or it may simply have been obscured on the gel by the high level of constitutive secretion of this chimera. Consistent with the TMD being the main determinant of Rhomboid-1-dependent cleavage, a chimera containing the Spitz extracellular domain with the TGFα TMD and cytoplasmic domain was not cleaved by Rhomboid-1; in the presence of Star, the O-glycosylated form of the full length protein accumulated in the cells. The converse TGFα:Spi-TMC chimera was also not detectably cleaved by Rhomboid.

Although this result appears at odds with the sufficiency of the Spitz TMD to confer Rhomboid sensitivity, the localisation of the TGFα:SpiTM and TGFα:Spi-TMC chimeras were quite distinct: the former was distributed throughout the secretory pathway, while the latter was tightly ER localised by virtue of the Spitz cytoplasmic domain. TGFα:Spi-TMC was therefore not exposed to Rhomboid-1 in the Golgi apparatus, explaining why no cleavage was detected.

Consistent with the idea that the TMD of Spitz confers Rhomboid-1 sensitivity, Spi:TGFαTMC is not cleaved by Rhomboid-1 whereas Spi-Δ53C is. The significance of the TMD is challenged, however, by published observations that deletion of the 15 amino acids between the extracellular face of the membrane and the EGF domain (Spi-Δ15) caused an apparent failure of Spitz cleavage (Bang and Kintner, 2000 supra). This construct activated EGF receptor signaling in a Xenopus explant assay in a Rhomboid and Star-dependent manner and it was concluded in this paper that the cleavage of Spitz was not the primary function of Rhomboid and Star.

However, in our assay Spi-Δ15 is cleaved in a Rhomboid-1 and Star-dependent manner, albeit at reduced efficiency, implying that the 15 residues between the membrane and EGF domain are not essential for Rhomboid-induced cleavage. Indeed, the reduced efficiency of cleavage of this construct could be entirely due to its diminished ability to be re-localised by Star. This result explains the discrepancy between our results and those presented previously (Bang and Kintner (2000) supra).

In summary, all the present results are consistent with the TMD of Spitz being necessary and sufficient for Rhomboid-1-dependent cleavage.

Rhomboid-1 Activity Does not Require Star

A prediction of our model is that a form of Spitz that was not retained in the ER would be cleaved by Rhomboid-1 in the absence of Star. To test this prediction, another Spitz:TGFα chimera was made, this time comprising Spitz with only its cytoplasmic domain replaced by the TGFα cytoplasmic domain (Spi:TGFα-C). The localisation of this construct resembled TGFα, although more of it was retained in the ER. In about 20% of cells it was visible in the Golgi apparatus and occasionally at the cell surface. This was never seen with Spitz, which is always ER-localised. Since Spi:TGFα-C has the Spitz lumenal domain, it was moved out of the ER by Star. Importantly, it was efficiently cleaved by Rhomboid-1 even in the absence of Star. The addition of Star did enhance Rhomboid-1 dependent cleavage, consistent with Star's ability to chaperone Spi:TGFα-C out of the ER.

This result demonstrates that the function of Star is to relocalise Spitz; it also demonstrates that Rhomboid-1-dependent cleavage does not require Star as a cofactor. Since Spi:TGFα-C is cleaved by Rhomboid whereas Spi:TGFα-TMC is not, and the only difference between them is their TMDs, this result provides indication that the Spitz TMD confers Rhomboid-1 sensitivity. These results were confirmed by the use of KDEL tagged Rhomboid which is localised in the ER as described below.

The Lumenal Domain of Star is Required for its Function

The lumenal domain of Spitz is sufficient to confer sensitivity to Star-dependent relocalisation so we tested whether the lumenal domain of Star was essential for its relocalising function. Three C-terminal truncations were tested which removed 291, 266 and 47 lumenal amino acids respectively (Star is a type 2 protein), and all abolished the ability of Star to relocalise Spitz significantly from the ER to the Golgi apparatus.

Consistent with this, these truncations were unable to mediate Star-dependent glycosylation of Spitz, or to induce Rhomboid-1-dependent cleavage. All three truncations were expressed at normal levels and with the same intracellular localisation as wild-type Star. Therefore, the lumenal domain of Star is necessary for its ability to relocalise Spitz, consistent with the idea that the primary interaction between Spitz and Star is lumenal.

The TMDs Contain the Core Function of Rhomboid-1

All members of the Rhomboid family have an N-terminal hydrophilic domain followed by the region containing the TMDs. In the case of Rhomboid-1, we have determined that the N-terminal domain is cytoplasmic. The lack of signal peptides in other Rhomboids provides indication that this topology is conserved. Despite the ubiquity of these N-terminal domains, they have no detectable sequence conservation, so their function is unclear.

The ability of the N-terminal alone (Rhomboid-1N) or the transmembrane domains without the N-terminal (Rhomboid-1ΔN) to promote Spitz cleavage was tested by expressing Rhomboid-1N and Rhomboid-1ΔN in the presence of substrate (GFP-Spitz) and Star in COS cells and assaying cleavage of substrate. The soluble cytoplasmic N-terminal had no activity, whereas Rhomboid-1ΔN cleaved Spitz, albeit with reduced activity.

Importantly, the Rhomboid-1ΔN cleavage was insensitive to 1:M and 10:M batimastat, confirming that the cleavage was not an artefact caused by metalloprotease-dependent cell surface shedding.

Figure 4:
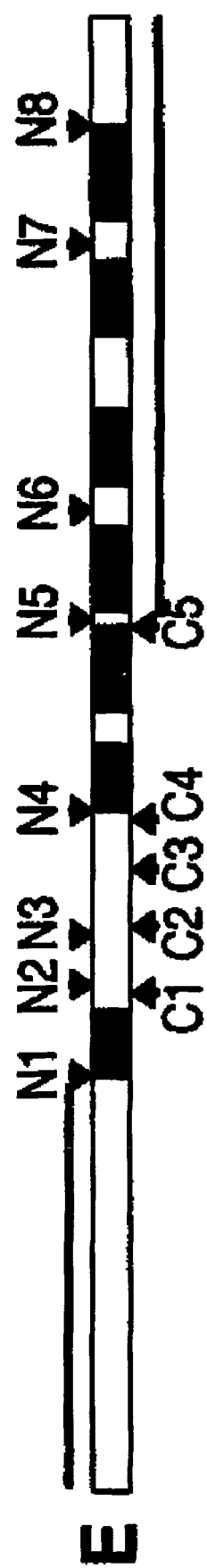

Identical results were obtained in vivo when these constructs were expressed in wings using the GAL4/UAS system (Brand and Perrimon (1993) Development 118 401-415): Rhomboid-1ΔN has similar activity to full-length Rhomboid-1 whereas Rhomboid-1N has no activity. To examine this further we made an extensive series of N and C-terminal truncations of HA-tagged Rhomboid-1 and tested their ability to promote Spitz cleavage in a standard COS cell assay. The only one of this series to retain some (reduced) activity was N8, in which the C-terminal lumenal domain of Rhomboid-1 was deleted. All others removed at least one TMD and all activity was lost (see Table 3 and FIG. 4).

Together, these results demonstrate that the core function of Rhomboid-1—its ability to promote Spitz cleavage—resides in the part of the protein with the multiple TMDs, not in the cytoplasmic N-terminus nor the lumenal C-terminus.

Rhomboid is a Proteolytic Enzyme

A key feature of enzymes is that they act catalytically in a reaction, at sub-stoichiometric levels. Conversely, reaction substrates and proteins with non-catalytic roles in a reaction behave stoichiometrically—reducing the amount of such proteins is expected to produce a proportional reduction in reaction products. Rhomboid-1 was tested in accordance with this principle for enzymatic behaviour in promoting the cleavage of Spitz.

The concentration of each of the three components of the cleavage reaction was titrated by reducing the amount of DNA transfected into COS cells. The total DNA was maintained at 1 μg per transfection, to ensure that the transfection efficiency remained constant. The amount of cleaved GFP-Spitz in the medium after 24-30 hours was determined by western blot.

Decreasing the amount of Spitz in the reaction was observed to have a linear effect on the amount of product. This is as expected, given that Spitz is the substrate for this reaction.

Reduction of Star was observed to have a strong effect on the overall efficiency of the Spitz cleavage reaction: the less Star is present, the less Spitz can be relocalised. This is consistent with the mechanism of Star acting as a chaperone protein that functions by interacting with Spitz and translocating it to the Golgi apparatus.

In contrast, reducing rhomboid-1 DNA by 10-fold and 100-fold actually increased its cleavage ability (by reducing Rhomboid-1's Golgi-disrupting effect). At 10,000-fold dilution (i.e. 0.025 ng of rhomboid-1 DNA per transfection), Rhomboid-1 is still effective at promoting Spitz cleavage.

An important control for this experiment was the demonstration that the amount of DNA transfected into the cells was directly proportional to the level of protein expressed (i.e. that HA-tagged Rhomboid-1 protein levels diminished in proportion to the input DNA). This was tested by probing western blots of cell lysates with anti-HA antibody to measure directly HA-Rhomboid-1 protein levels. Even at the first dilution in the series (10-fold), the level of Rhomboid-1 was reduced to below detectable. This confirms that Rhomboid-1 efficiently promotes proteolytic activity at extremely low levels. The contrast between this property of Rhomboid-1 and the sensitivity of Star and Spitz to reduction in their levels, demonstrates that Rhomboid functions sub-stoichiometrically, the hallmark of an enzyme.

Similar titration experiments were performed in other cell lines (CHO, NIH3T3 and HeLa) and the same results were obtained, implying that the sub-stoichiometric function of Rhomboid-1 is a general property of this protein.

If Rhomboid-1 was acting as an enzyme, certain residues within the Rhomboid 1 sequence would be expected to form the catalytic site. The activity of an enzyme would be especially sensitive to mutagenesis of residues in this catalytic site: in fact their alteration should completely abolish enzymatic activity, if they are genuinely part of the catalytic function.

In contrast, residues that are involved with other aspects of Rhomboid-1 function (e.g. binding to other proteins, protein conformation) may be less sensitive to alteration.

All residues that are highly conserved within the Rhomboid family (excepting a few glycines, which would be predicted not to have a catalytic function) were individually mutated in Rhomboid-1. The ability of these mutated forms of Rhomboid-1 to promote Spitz cleavage was then tested in the COS cell assay by western blot analysis of cleaved GFP-Spitz in the medium.

The expression of the mutant forms (which were all HA-tagged) was confirmed by probing cell lysates with anti-HA antibody: all were expressed at comparable levels. Of the 13 highly conserved residues, only 6 were essential for Rhomboid-1 function. Alteration of any one of these six to alanine (W151, R152, N169, G215, S217, H281) completely abolished Rhomboid-1 activity. Given the sensitivity of this assay (even a 1:1000 dilution of the normal input amount of rhomboid-1-HA DNA had detectable activity), it can be concluded that each of these single mutations reduced the proteolytic function by at least 1000-fold.

Mutation of other conserved residues led to a detectable but incomplete reduction in Rhomboid-1 function (R188, G218) or activity indistinguishable from wild-type function (S155, H160, H165, E181, Y193). Note that the assay is so sensitive to Rhomboid function that these latter cases might reduce activity significantly without leading to a detectable reduction in cleaved Spitz in the medium. Therefore, despite their activity in this assay, these residues may be important for some aspect of Rhomboid-1 function, but they cannot be essential for catalysis itself.

Rhomboid-1 is a Serine Protease

Rhomboid-1 has been shown to possess the properties of a protease that cleaves Spitz. However, since there are no well-conserved cysteine or aspartic acid residues in the Rhomboid proteins, Rhomboid-1 is unlikely to be a cysteine or aspartyl protease. The other two classes of known proteases are metalloproteases and serine/threonine proteases.

Rhomboid-1 has a number of conserved histidine residues that could act to coordinate a metal ion, which might indicate that it is a metalloprotease. However, the mutagenesis analysis described above indicates that most of these residues are not part of the catalytic mechanism. Furthermore, Rhomboid-1-dependent cleavage of Spitz has been found to be insensitive to the potent inhibitors of metalloproteases, batimastat and ilomostat. The batimastat assay was performed over a range of Rhomboid-1 concentrations (2.5, 0.25 and 0.025 ng Rhomboid DNA per 35 mm well of transfected COS cells in 1 $\mu$M and 10 $\mu$M Batimastat) to search for any batimastat sensitivity, even at concentrations where Rhomboid-1 is limiting.

Under all conditions tested, batimastat at 1:M and 10:M had no effect on Rhomboid-1-dependent cleavage, confirming the conclusion that the cleavage of Spitz is not catalysed by a metalloprotease.

The site directed mutagenesis described above focussed our attention on a cluster of residues in TMD4 of Rhomboid-1. In the GASGG SEQ.ID. 6 motif, the first glycine (G215) and the serine (S217) are both essential for catalytic activity. This sequence is conserved in almost all Rhomboid homologues that exist in sequence databases. Strikingly, it is similar to the GXSGG SEQ.ID. 8 sequence in many serine proteases including chymotrypsin and trypsin, where the serine is the active residue in the hydrolytic reaction itself. In these serine proteases, the first glycine in this motif also has an important function (though it is not a component of the catalytic triad), hydrogen bonding to the peptide backbone of the substrate. The serine protease catalytic triad also includes a histidine. In Rhomboid-1 histidine 281, in TMD6, is one of the other essential residues and it is predicted to be in a similar position in the lipid bilayer as the putative catalytic serine. They could therefore form part of a serine protease active site. Such a serine protease active site would be entirely novel, as it occurs within a lipid bilayer.

The third residue of the serine protease catalytic triad is an aspartate; there are no conserved essential aspartates in Rhomboid-1.

Interestingly, asparagine-169 in TMD2 of Rhomboid-1 is essential; it is predicted to reside at a similar level in the bilayer as serine-217 and histidine-281 and therefore is a candidate to be involved in Rhomboid-1 catalysed proteolysis. A hydrophobic cysteine protease is known in which the aspartate of the catalytic triad is replaced with an asparagine (Vernet et al (1995) J. Biol. Chem. 270 16645-16652). Cysteine proteases have very similar catalytic mechanisms to serine proteases, so this provides indication that N-169 substitutes for the aspartate in the Rhomboid catalytic triad.

The function of the last two essential residues (W151 and R152) has not been established. They are predicted to be in the lumenal loop between TMD1 and TMD2.

The experiments described herein demonstrate that Rhomboid-1 is a novel serine protease that cleaves substrates within their transmembrane domains and that R152, G215, S217 and H281 are the key catalytic residues, forming the catalytic centre and/or essential docking sites, with W151 and N169 also being of some importance.

This is strongly supported by our observation that Rhomboid-1-dependent cleavage of Spitz was not inhibited by specific inhibitors of metalloproteases but was sensitive to serine protease inhibitors. We performed the standard cleavage assay in the presence of a panel of inhibitors.

No inhibition of Rhomboid activity was observed with the following inhibitors; cysteine protease inhibitors E64d (50:

M) and leupeptin (100:M) (Salvesen, G. S., and Nagase, H. (2001). Inhibition of proteolytic enzymes. In Proteolytic Enzymes, R. Beynon, and J. S. Bond, eds. (Oxford, Oxford University Press), calpain inhibitor PD150606 (Wang, K. K. et al. (1996). Proc Natl Acad Sci USA 93,6687-6692.), aspartyl protease inhibitor pepstatin A (50:M) (Salvesen, G. S., and Nagase, H. (2001). Inhibition of proteolytic enzymes. In Proteolytic Enzymes, R. Beynon, and J. S. Bond, eds. (Oxford, Oxford University Press), gamma secretase inhibitor I (25:M) (Hartmann, T. et al(1997). Nat Med 3, 1016-1020), and metalloprotease inhibitors batimastat (British Biotech) and ilomostat (Calbiochem).

However, two serine protease inhibitors (TPCK and 3,4-DCI) were observed to strongly inhibited the reaction (10-100:M). Importantly, this concentration of DCI and TPCK did not effect the expression or secretion of an artificially truncated form of Spitz (the extracellular domain, missing the transmembrane and cytoplasmic domain). This indicates that DCI and TPCK affect Spitz cleavage itself, not its expression or secretion. This provides direct evidence that Rhomboid-1 is a novel serine protease. This being so, it is the first described serine protease in which the catalytic site occurs within the lipid bilayer of a membrane.

Human Rhomboid Homologues

The programs tblastn and blastp were used to search public sequence databases for Rhomboid genes. The following three human sequences, which had greater than 40% similarity to the *Drosophila* rhomboids, were identified (with GenBank accession numbers);

1) XM_007948, NM_003961, AJ272344 (different numbers represent different submissions of the same gene); this corresponds to the RHBDL gene identified and published by Pascall and Brown (FEBS Lett. 429, 337-340, 1998).
2) NM_017821; this gene was identified in the human genome project as a predicted gene and full-length cDNAs have been isolated. Although it was annotated as having similarity to *Drosophila* rhomboid, it has otherwise not been named or characterised. The name RHBDL2 has been officially accepted by the human gene nomenclature committee.
3) BE778475; this is only an incomplete cDNA; the gene was not identified or annotated in the human genome project. Nor was the sequence annotated as having any rhomboid similarity. Using the Genemark program (Borodovsky M. and McIninch J. Computers and Chemistry (1993) 17 19 123-133) we searched the surrounding genomic DNA sequence to identify the full length sequence. This full length sequence is shown in FIG. 7.

The full-length gene sequence shows significant similarity with RHBDL-1 and RHBDL2 over its entire length (52.6% identity, 60.2% similarity to RHBDL1; 35.0% identity, 47.7% similarity to RHBDL2; 34.7% identity, 45.7% similarity to *Drosophila* rhomboid-1). The name RHBDL-3 has been officially accepted for this gene. Importantly, the RHBDL3 gene product contains all the conserved residues shown to be catalytically essential for Rhomboid protease function. The gene therefore encodes a true Rhomboid with proteolytic activity.

Substrate Specificity of *Drosophila* Rhomboids

The ability of three other *Drosophila* Rhomboids to cleave Spitz and two other *Drosophila* TGFα-like ligands, Keren and Gurken was assessed.

*Drosophila* Rhomboid-1, -2, -3 or -4 were expressed in COS cells and their ability to cleave the ligands was compared over a range of Rhomboid expression levels (from 25 ng to 0.05 ng per transfection). Cleavage was assayed by western blotting of the 24 hour-conditioned medium for the presence of soluble GFP-Spitz. All four Rhomboids cleaved Spitz efficiently using the GAL4/UAS system (Brand & Perrimon supra). We have confirmed this result in vivo: the ectopic expression of all four Rhomboids leads to similar phenotypes typical of EGF receptor hyperactivity, such as rough eyes and extra wing vein material. It can therefore be concluded that the proteolytic activity of Rhomboid-1 has been conserved in all four of the *Drosophila* Rhomboids tested. Note that in all cases, the residues identified herein as being essential are conserved, as is the overall predicted structure of the protein, but otherwise there is quite wide divergence of sequence homology, especially between Rhomboids 1 and 4.

The ability of *Drosophila* Rhomboids 1 to 4 to promote the cleavage of two other TGFα-like *Drosophila* ligands, Gurken and Keren was also analysed in a COS cell cleavage assay and in a similar assay performed in *Drosophila* S2 tissue culture cells. Gurken was efficiently cleaved by all four Rhomboids tested but unlike Spitz, the cleavage efficiency was independent of Star. All four Rhomboids fully cleaved the full length form of Gurken but Rhomboid-1 consistently produced two intracellular cleaved products, whereas Rhomboids 2 to 4 produced only one intracellular band. The fact that all four Rhomboids cleave Gurken supports the earlier conclusion that they all have the same core proteolytic activity, but the observation that Rhomboid-1 causes a different pattern of cleavage indicates that their action is not identical.

This specificity is further highlighted in the case of Keren cleavage. Again, all four Rhomboids promoted cleavage, but in this case, the differences were more pronounced.

In the absence of Star, Rhomboids 1 and 2 led to inefficient cleavage of Keren; the level of cleavage was so low that it could only be detected as a minor novel band in the cell lysate (unlike Gurken, most of the detectable Keren remained uncleaved) and it did not accumulate to detectable levels in the medium.

In contrast, Rhomboids 3 and 4 catalysed more efficient Star-independent cleavage and secretion of Keren; the cleaved product was visible in the cell lysate and also accumulated substantially in the medium.

In the presence of Star, the overall efficiency of cleavage and secretion of Keren was enhanced but the differential between Rhomboids 1 and 2 on one hand and Rhomboids 3 and 4 on the other, was maintained, as assayed by the intensity of the cleaved band in the cell lysates.

Interestingly, as with Gurken, Rhomboid-1 cleavage produced two products in the cell lysates, while Rhomboids 2 to 4 produced a single band. On the basis of these results we conclude that Rhomboids 3 and 4 are much more efficient than Rhomboids 1 and 2 at cleaving Keren; and that Rhomboid-1 has a distinct cleavage action, apparently cleaving Keren at two sites. Again, these results indicate that there is some substrate specificity between different Rhomboids.

Proteases often display specificity for their substrates to achieve the precision required to regulate biological processes (as reviewed in Perona, J. J., and Craik, C. S. (1997). *J Bioi Chem,* 272: 29987-90). Despite cleaving Spitz, Gurken and Keren, Rhomboid-1 could not cleave other type-I membrane proteins including *Drosophila* EGF receptor, *Drosophila* Delta, human TGN38 (Luzio, J. P., Brake, B., Banting, G., Howell, K. E., Braghetta, P., and Stanley, K. K. (1990) *Biochem J,* 270: 97-102) and human TGFα.

Furthermore, analysis of Spitz cleavage in the ER by Rhomboid-1-KDEL provides indication that Rhomboid-1 alone is responsible for this specificity. KDEL SEQ.ID. 5 is an ER-retention signal that retains the KDEL-tagged Rhomboid-1 polypeptide in the ER. Cleavage by Rhomboid-1-

KDEL does not rely on Spitz trafficking by Star, and this allows a direct test of whether Star has a secondary role in substrate presentation to Rhomboid-1.

Although it has been proposed that Star physically binds to both the Spitz substrate and the Rhomboid-1 protease (Hsiung, F., Griffis, E. R., Pickup, A., Powers, M. A., and Moses, K. (2001) *Mech Dev*, 107: 13-23) (Tsruya, R., Schlesinger, A., Reich, A., Gabay, L., Sapir, A., and Shilo, B. Z. (2002). *Genes Dev*,16: 222-34.), the amount of intracellular cleavage catalysed by Rhomboid1-KDEL was not observed to be enhanced when Star was co-expressed with various forms of Spitz. Therefore the specificity and proteolytic activity of Rhomboid-1 is fully independent of Star.

These observations indicate that Rhomboid-1 is highly selective in its choice of substrate and demonstrate that the specificity in Spitz cleavage is determined by Rhomboid-1 alone.

Cleavage of Spitz by Human RHBDL2

A full-length cDNA for Human RHBDL2 was listed in the Japanese NEDO human cDNA sequencing project (clone number FLJ20435).

The Human RHBDL2 cDNA was expressed in COS cells and its ability to induce Spitz cleavage in the presence of Star was analysed. GFP-Spitz, Star and Human RHBDL2 were expressed in COS cells. Accumulation of GFP-Spitz in the medium was assayed in the presence of 10 μM batimastat (to inhibit background metalloprotease activity). Under these conditions, human RHBDL2 efficiently catalysed GFP-Spitz cleavage.

This provides further demonstration that the core proteolytic function of Rhomboid is conserved between *Drosophila* and humans, as is further evidenced by the conservation of the key catalytic residues. This conservation of sequences between *Drosophila* Rhomboid-1 and RHBDL2 (all the key catalytic residues are identical) provides further indication that the these proteases work by the same mechanism.

The six residues found to be important for Rhomboid-1 activity were mutated in human RHBDL2. Mutation of R111, G174, S176 or H239 (numbered according to the human RHBDL2 sequence) to alanine completely abolished the proteolytic cleavage of Spitz by human RHBDL2. Mutation of W110 and N128 reduced, but did not abolish proteolytic activity. The conservation of key residues in RHBDL2 demonstrates that the proteolytic cleavage of Spitz by RHBDL2 occurs through the same mechanism as proteolytic cleavage by Rhomboid-1.

The catalytic serine (typically GA<u>S</u>G SEQ.ID. 4, although variants at positions 2 and 4 exist) motif is shown herein to be conserved as the catalytic centre of an intramembrane protease in members of the family well separated in evolution (Rhomboid-1, human RHBDL2, bacterial and yeast RHBDLs). The provides indication that the same enzymatic activity is conserved across the whole family of conserved Rhomboid-like proteins, which are shown to be related intramembrane proteases.

Truncated Forms of Rhomboid-1 Act as Dominant Negatives

A truncated form of Rhomboid-1 was made comprising residues 1 to 149 of Rhomboid-1, the N-terminal cytoplasmic domain plus the first TMD and part of the first extracellular loop (Rho-1-NTM1).

When co-expressed with Star and full-length Rhomboid-1 in the COS cell Spitz cleavage assay, the truncated Rhomboid-1 inhibited the ability of the wild-type protein to promote GFP-Spitz cleavage. There are two obvious explanations for this result: either the truncated Rhomboid is acting as a dominant negative construct (i.e. it is specifically interfering with the Rhomboid-1 cleavage event) or it might be non-specifically disrupting the cells' viability or ability to secrete proteins.

Rho-1-NTM1 did not interfere with TGFα synthesis or secretion, which was indistinguishable from a control. Therefore, this N-terminal fragment of Rhomboid-1 has the ability to inhibit Rhomboid-1-dependent Spitz cleavage quite specifically, providing indication that it is indeed a dominant negative form of the protein.

The dominant negative activity of this Rhomboid-1 fragment was confirmed in vivo by expressing it in *Drosophila* using P-element mediated transformation. When expressed in the developing eye using the Gal4/UAS system (Brand and Perrimon), it caused cell death, a phenotype associated with loss of Rhomboid-1 and Rhomboid-3 function.

Since the overall structure and topology of proteins of the Rhomboid family is well conserved, and since the catalytic mechanism appears to be conserved (four distinct *Drosophila* Rhomboids have the same core catalytic activity and the potential catalytic residues we have identified are conserved throughout most of the family), it follows that the dominant negative activity of similar N-terminal fragments of other Rhomboids may be employed. This may provide techniques for determining the role of Rhomboids from any species, regardless of whether mutations in the genes exist, as well as for manipulating Rhomboid activity for practical purposes.

Genetic analysis has implied that Star and Rhomboid-1 are the primary regulators of *Drosophila* EGF receptor activation but their mechanisms have remained elusive until now (reviewed in Schweitzer and Shilo, (1997) Trends in Genetics 13, 191-196; Wasserman and Freeman, (1997) Cell 95, 355-364; Klämbt, (2000) Curr Biol 10, R388-91). We have now determined the mechanism of each of these molecules: Star is necessary for the export of the activating ligand Spitz from the ER to the Golgi apparatus. There, Spitz encounters Rhomboid-1, which is a transmembrane serine protease which cleaves the ligand.

Cleavage itself is a new variation of regulated intramembrane proteolysis (Brown et al. (2000) Cell 100, 391-8) which occurs within the Spitz TMD. Once cleaved, the soluble lumenal ligand fragment is secreted from the cell to trigger the activation of the EGF receptor. Thus the rate limiting steps of the *Drosophila* EGF receptor signaling pathway occur primarily at the level of ligand translocation and proteolytic cleavage.

Spitz Recognition and Cleavage

To determine the location of Spitz cleavage, the size of the Rhomboid-1-cleaved product was compared with the size of Spitz fragments expressed from artificially truncated open reading frames. The cleaved product was detectably larger than a form of Spitz truncated immediately N-terminal to the TMD (residue 139), but smaller than a truncation at residue 149, which is ⅔rds into the TMD (from the lumenal surface). Therefore Spitz is cleaved between residues 139 and 149. Since the resolution of this assay is approximately 5 residues, this places the cleavage site at approximately residue 144, within the lumenal half of the TMD. This is the same 'height' within the TMD as the proposed Rhomboid-1 active site. No other intramembrane protease is known to cut TMDs towards their lumenal/extracellular side.

Figure 6:
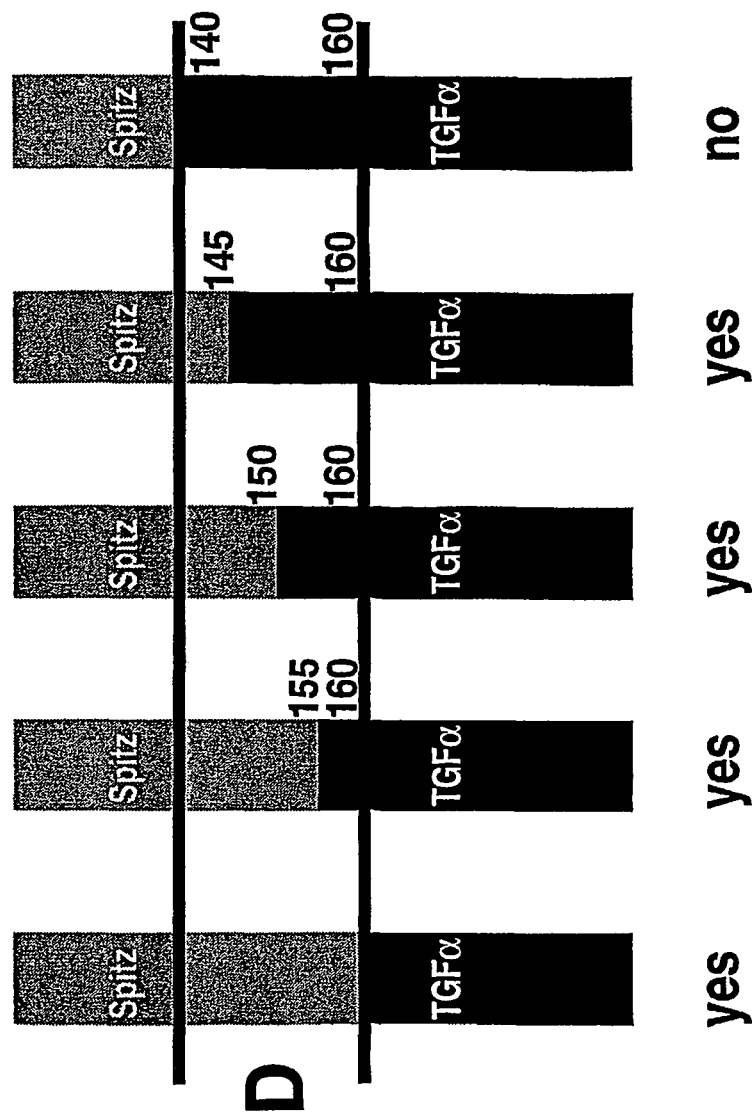

Spitz TMD was sequentially replaced with that of TGFα in four nested segments starting from the cytoplasmic end (see FIG. 6). This was done in a chimeric Spitz molecule that had the TGFα C-terminus to confer a Star-independent Golgi localisation. Replacing the bottom ¼ (Spitz residues 155-160), 2/4 (residues 150-160), or ¾ (residues 145-160) of the Spitz TMD with that of TGFα did not affect cleavage by Rhomboid-1. However, replacing the remaining 5 residues (residues 140-160) abolished cleavage. Star was not used in these assays, and they were done in the presence of batimastat to remove background cleavage by cell-surface metalloproteases.

To exclude the possibility that replacing the entire Spitz TMD with that of TGFα resulted in masking of the Rhomboid-1 recognition site by TGFα-specific binding proteins rather than by loss of the recognition site, a similar analysis with a different TMD was performed: this time the Spitz TMD was sequentially replaced with segments from an unrelated TMD—from the mammalian protein TGN38. This yielded identical results, confirming that the five TMD residues of Spitz closest to the lumenal face contain the site that Rhomboid-1 recognises.

This analysis pinpointed Spitz residues 140-144 (IASGA) SEQ.ID. 1 as containing the principal Rhomboid-1 recognition site; when replaced by the equivalent sequence from TGFα (ITALV)SEQ.ID.9, this abolished cleavage by Rhomboid. In a primary analysis, each of these was mutated individually in wild-type Spitz. Only the A141T, G143L, and A144V mutations reduced Rhomboid-1 cleavage, each doing so by about 3-5 fold. The G143L mutation conferred the strongest effect, while the S142A mutation had no detectable effect on Spitz cleavage.

Computer predictions of the Spitz TMD (e.g. with the program TMHMM—Krogh, A., Larsson, B., von Heijne, G. and Sonnhammer, E. L. (2001). *J Mol Biol*, 305, 567-580.) indicate that the TMD actually extends two residues N-terminal of the sequence replaced in the Spitz/TGFα chimera series described above. Therefore, in conjunction with the results of the TGFα chimeras, the residues ASIASGA SEQ.ID. 2 (residues 138-144) were analysed for their role in determining Spitz cleavage.

First, in order to test which of the residues in the critical region of Spitz were responsible for recognition by Rhomboid-1, each of the residues found in Spitz was introduced individually into the TGFα TMD of the uncleavable Spitz-TGFα chimera (i.e. Spitz with residues 140-160 replaced by the equivalent residues from TGFα). Remarkably, substitution of only Spitz residue G143 restored cleavage of this chimeric substrate, while substitution of both G143 and A144 resulted in more efficient cleavage. Thus, Rhomboid-1 appears to target this GA motif within Spitz. Intriguingly, the exact position of this GA motif within the substrate TMD is not absolutely constrained as Rhomboid-1 could cleave Spitz with the GA motif displaced one residue and three residues further into the TMD.

Figure 9:
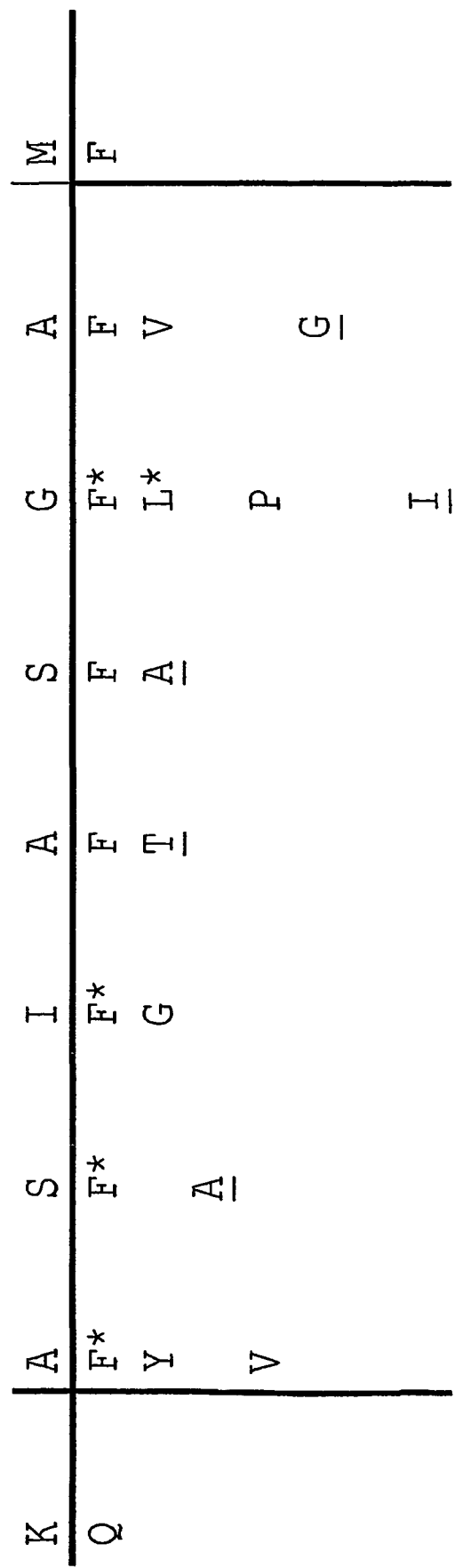
FIG. 9 shows the effect of mutation of residues in the Spitz TMD on cleavage efficiency SEQ.ID. 18-38.

Second, in a complementary approach similar to the primary analysis described above, all of the critical region residues were mutated singly in wild-type Spitz. The ability of these mutant forms of Spitz to act as substrates for Rhomboid-1 was assessed using Rhomboid-1-KDEL (which allows cleavage in the ER to be assayed and avoids variation of secretion efficiency causing misleading results). This is significant because since many of the mutated forms of Spitz differ in their ability to be secreted. Under these conditions, the amount of cleavage was dependent on the quantity of Rhomboid-1-KDEL in cells, and it was possible to use a concentration of Rhomboid-1-KDEL that resulted in approximately 50% cleavage such that mutations that both enhanced and suppressed cleavage could be identified. The results are summarised in FIG. 9, where the wild-type sequence is shown along the top of the table and the mutations tested are shown below their respective wild-type residues. Asterisked mutations abolished Spitz cleavage; unlabelled mutations had little or no effect; and those underlined enhanced cleavage. The vertical lines show the limits of the experimentally-determined critical region.

This analysis of Spitz mutants revealed two further characteristics of the critical region. First, although the first three positions could not accommodate large, disruptive residues such as phenylalanine, the presence of such residues was less important in the second half of the critical region. Consistent with the restoration analysis, G143F was the only residue of the second half of the critical region to be sensitive to phenylalanine mutagenesis. These results suggest that, in addition to G143, the residues of the top half of the critical region may have a role in recognition by Rhomboid-1. Interestingly, the disruptive nature of the A138F mutation was likely to be due to increasing hydrophobicity rather than size at this site since a tyrosine substitution was cleaved efficiently. Thus, the first few residues of the Spitz TMD may need to be limited in hydrophobicity, perhaps to allow water to pass into the Rhomboid active site. Secondly, four mutations were isolated that enhanced cleavage by Rhomboid-1, and these were residues that are generally thought to destabilise helices. Two of these residues were very small; mutation of the A144 of the GA motif to the smaller residue glycine and mutation of S139 to the smaller alanine residue both enhanced cleavage. Mutation of residues 141 and 143 to β-branched residues threonine and isoleucine, respectively, also enhanced cleavage. Thus, certain small and β-branched residues were effective for enhancing cleavage by Rhomboid-1.

Collectively, these results indicate that Rhomboid-1 does not recognise a specific sequence, but rather a structural determinant, apparently a common disordered conformation. Small residues such as those of the GA motif are not as constrained in their conformation as larger residues, and are thus known to destabilise rigid structures such as helices (Chou, P. Y., and Fasman, G. D. (1978). *Annu Rev Biochem*, 47: 251-76. Parker, M. H., and Hefford, M. A. (1997) *Protein Eng*, 10: 487-96. Liu, L. P., and Deber, C. M. (1998) *Biopolymers*, 47: 41-62. Butcher, D. J., Luo, Z., and Huang, Z. (1999). *Biochem Biophys Res Commun*,265: 350-5.). Furthermore, β-branched residues also have lower propensity to be in helical structures. Thus, the critical region of the Spitz TMD may be able to adopt a non-helical conformation, in contrast to many TMDs.

*Drosophila* Rhomboids 2, 3,4 and human RHBDL-2 were tested for protease activity against the uncleavable form of Spitz (in which residues 140-160 replaced by the TGFα TMD), and against the TGFα TMD with a restored G143. Rhomboids 2,3, and RHBDL behaved exactly as Rhomboid-1: they could not cleave the TGFα TMD, but did cleave when only G143 was added back. This indicates that these Rhomboids all use the same mechanism to recognise polypeptide substrate.

Rhomboid-4 Specificity

*Drosophila* Rhomboid-4 is distinct from the other Rhomboid polypeptides that have been tested (e.g. *Drosophila* Rhomboids 1,2,3 and human RHBDL2). Whilst many Rhomboid polypeptides have defined and restricted specificities for substrate recognition, Rhomboid-4 cleaves all the polypeptide substrates tested so far, including Spitz, Gurken, Keren, human TGFα, the 'non-cleavable' Spitz/TGFα chimera, and the completely unrelated *Drosophila* EGF receptor.

Therefore, unlike the other Rhomboid polypeptides, Rhomboid-4 is a broad spectrum intra-membrane protease which is capable of cleavage of the TMD of a wide range of proteins.

Bacterial Rhomboids

Although the Rhomboid family does not possess high overall homology, bioinformatic tools as described herein, such as PFAM and psi-Blast, may be used to identify family members in all branches of evolution.

Table 1 provides examples of members of the Rhomboid family identified in this way. Intra-membrane protease activity similar to that of *Drosophila* and human Rhomboid polypeptides, has been also observed for other members of the Rhomboid family.

Rhomboid polypeptides have been cloned from the following bacteria: *Escherichia coli* (gene: glpG, BVECGG), *Providencia stuartii* (gene: A55862), *Pseudomonas aeruginosa* (gene: B83259), *Thermotoga maritima* (genes: AAD36164 and AAD35669), *Bacillus subtilis* (genes: ydcA, G69772 and yqgP, BAA12519), *Bacillus halodurans* (gene: BABO5140), *Pyrococcus horikoshii* (gene: E71025), and *Aquifex aeolicus* (gene: AAC07308).

Using the standard COS cell cleavage assay (but transfecting 100 ng of Rhomboid DNA per 35 mm well) rhomboids from *E coli, Providencia* and *Pseudomonas* (all of which are human pathogens) and *B. subtilis* yqgP (gram positive) have been observed to cleave the *Drosophila* substrates Spitz, Gurken and Keren.

Thus functional Rhomboid polypeptides may be identified by bioinformatic techniques. Even bacterial rhomboids, which are more than a billion years diverged from humans and flies, have the same core catalytic activity; they are intramembrane proteases. This demonstrates that Rhomboids are a functional enzyme family that share the same core activity of intramembrane serine proteases. Furthermore, substrate specificity has been conserved between *Drosophila* Rhomboids 1-4, human RHBDL2 and a number of bacterial rhomboids.

Yeast Rhomboid Polypeptides

*Saccharomyces cerevisiae* Rhomboid polypeptides YGR101w and YPL246c were cloned and their function investigated. YGR101w regulates mitochondrial function while YPL 246c appears to be involved in endocytosis.

Yeast Rhomboid-1 (YGR101w)

Expression of GFP-tagged Yeast Rhomboid-1 and co-staining with mitochondrial markers indicates that the protein is expressed not in the Golgi apparatus but in the mitochondria. This was also predicted from the Yeast Rhomboid-1 sequence using MITOPROT (Claros & Vincens,1996, Eur J. Biochem. 241,779-786).

Deletion of ygr101w causes slow growth and morphological disruption of mitochondria, as indicated by EM analysis and fluorescent staining with mitochondrial markers. Moreover, deletion mutants fail to grow in conditions in which glycerol is the only carbon source. This is a classic sign of disruption of respiratory metabolism.

Our results indicate that these phenotypes are caused by the absence of YGR101w serine protease activity because replacement of the wild type gene with a catalytically dead form (GAGG SEQ.ID. 10 instead of GASG SEQ.ID. 4 around the active serine) fails to rescue the cell, while replacement with a wild-type form does successfully rescue the cell.

The substrate for yeast Rhomboid-1 may be one or more of the following, which are all single TMD mitochondrial proteins with single TMDs, which act as soluble, cleaved proteins:

i) PET100/YDR079W-protein involved in assembly of cyt c oxidase,
ii) OSM1/YJR051W -oxidoreductase protein involved in osmolarity regulation,
iii) MGM1/YOR211C-dynamin related protein involved in membrane fusion,
iv) MCR1/YKL150W-oxidoreductase protein involved in oxidative stress resistance,
v) CCP1/YKR066C-oxidoreductase protein involved in cell stress.

Significantly, MGM1 and PET100 mutants share the YGR101W phenotype, making these favoured candidates for YGR101w substrates.

Yeast Rhomboid-2 (YPL246c)

Yeast Rhomboid-2 (YPL246c) is expressed in the secretory pathway and its deletion impairs membrane and vesicle dynamics. Electron microscopy indicates that YPL246c knockouts have extraneous membrane fragments in their cytoplasm. Furthermore, although in the wild-type the SNARE SNC1 recycles between the Golgi apparatus and the plasma membrane via endosomes (Lewis M. et al (2000) Mol. Cell. Biol. 11 23-28), this recycling is disrupted in the knockouts.

The uptake of the fluorescent dye FM4-64 (Vida and Emr (1995) J. Cell Biol. 128 779-792) is also impaired in knockouts.

This evidence indicates a defect in endocytosis, although other aspects of the secretory/endocytic pathway could be also disrupted. The mutant phenotype can be rescued by Knock-in of the wild-type YPL246c gene but not by a catalytically dead form (GASG SEQ.ID. 4 to GAGG SEQ.ID. 10). This demonstrates that its function is dependent on the Rhomboid-like intramembrane serine protease activity.

Zebrafish (*Danio rerio*) RHBDL2

To investigate the role of vertebrate Rhomboids, the zebrafish homologue of human RHBDL2 (sequenced from cDNA clone 2652120, GenBank accession number AW422344) was knocked out using the standard technology of antisense morpholino oligonucleotides (reviewed in Heasman J. Dev Biol. Mar. 15, 2002;243(2):209-14), which allows the rapid removal of a gene function. Zebrafish embryos are a common model system as their embryonic development is easily observed.

RHBDL2 was observed to be expressed in a dynamic and specific expression pattern during embryogenesis. Knockout with the anti-sense morpholino oligo TCTTGCTCTTCGGT-GTCATTATCGC SEQ.ID. 7 leads to specific defects in the brain, the otic placode and the tail. These regions correspond to sites of RHBDL2 gene expression.

These results provide the first indication of a significant, non-redundant function of vertebrate rhomboids and indicate that other vertebrate rhomboids, in particular mammalian rhomboids, will also participate in physiologically-significant processes.

Active Form of Rhomboid-1

All known intramembrane proteases are synthesised as inactive zymogens which are activated by endoproteolytic cleavage.

Analysis of tagged Rhomboid-1 revealed that the predominant form in cells was full length, as estimated by apparent molecular weight, but a cleaved form was also apparent in both COS and S2 cells.

The fact that the full length form was the predominant form was established by demonstrating that western blots with anti-HA (the epitope tag) of N and C-terminal tagged forms showed the same, full-length product—the only band that these tagged forms could have in common is the full length protein.

The size of the proteolytic fragment was compared to a set of truncated versions of Rhomboid-1, and this showed that the cleavage occurred within the lumenal loop between TMD 1 and 2.

Mutations in conserved amino acids in the cytoplasmic regions of TMDs 2 and 3 abolished this cleavage, but these non-cleavable proteins had full Spitz proteolytic activity, demonstrating that the full length forms of Rhomboid-1 are active.

Mutation of Rhomboid-1 active site residues abolished its protease activity, but did not affect the endoproteolysis of Rho itself, showing that this cleavage is not autocatalytic (i.e. Rhomboid-1 activity is not responsible for its own cleavage).

These results show that full-length Rhomboid-1 protein is active and, unlike other intramembrane proteases, it does not require proteolytic activation, either by its own activity or by other proteases. This has practical advantages in producing active enzyme in vitro, as simple expression of the protein is sufficient for activity.

Function of Star

In the absence of Star, Spitz is retained in the ER. This explains why the domain of EGF receptor activation is much narrower than the expression pattern of Spitz (Rutledge et al., (1992) Genes Dev. 6, 1503-1517; Gabay et al., (1997) Science 277, 1103-1106), and why ectopic expression of full-length Spitz does not activate the receptor (Schweitzer et al., 1995 supra). Star, a protein with a single TMD (Kolodkin et al., (1994) Development 120, 1731-1745), is necessary to translocate Spitz into the Golgi apparatus. The principal interaction between Spitz and Star occurs between the lumenal domains of the two proteins and this interaction counteracts the cytoplasmic Spitz ER retention.

Star does not act by specifically blocking the ER retention signal which is present in the Spitz cytoplasmic domain. Two chimeras containing the Spitz lumenal domain with the human TGFα C-terminal domain are not held in the ER in COS cells, but are nevertheless re-localised by Star. This provides indication that Star actively exports Spitz from the ER.

*Drosophila* genetics indicates that Star and Rhomboid-1 are both prime regulators of EGF receptor activity: they both appear to be necessary and they cannot replace each other (Guichard et al.,(1999) Development 126, 2663-76). It has not been possible until now to separate their functions. Our results explain their co-dependency and synergy, and also provide a clear mechanistic distinction between Star and Rhomboid-1.

Star is not necessary for Rhomboid-1-dependent proteolysis itself, as an enzymatic cofactor. The Spi:TGFα-C chimera leaves the ER independently of Star and can be cleaved by Rhomboid-1 in the absence of Star. Therefore the sole function of Star in the activation of Spitz is to chaperone it from the ER to the Golgi apparatus, thereby delivering it to Rhomboid-1.

Optimised Substrate Design

To simplify and optimize assays using Rhomboid polypeptides, a chimeric substrate was designed to be cleaved more efficiently than any of the natural substrates and have a broad specificity for a range of rhomboids that cleave *Drosophila* Spitz (e.g. all *Drosophila* rhomboids, human RHBDL2, *E. coli, Providencia* and *Pseudomonas* Rhomboid).

The TGFα-GFP-Spi-TGFα 'ideal substrate' construct (here termed ST) was constructed using standard techniques from the following (nucleotide coordinates): 1-34 is TGFα UTR, 35-130 (35 is first A of ATG) is TGFα signal/propeptide sequence up to the BsiWI site (which we engineered into the sequence and into which any tag can be cloned) then GFP, and the remainder is TGFα with the Spitz 15aa and TMD (1045-1159). This insert was cloned into the pcDNA3.1(+) vector with HindIII (5') and XbaI (3').

The ST substrate is cleaved very efficiently in mammalian cells and is secreted very efficiently. This is significant because several known substrates can be cleaved but are not then efficiently released into the medium and secretion is an important requirement for any high throughput assay. The ST substrate is Star-independent (since its cytoplasmic domain derives from human TGFα), which provides a simpler and more direct assay and is tagged to provide for assay automation.

A convenient restriction site (BsiWI) has been engineered in the N-terminal domain of the constructs used in the present experiments into which tags, such as GFP, luciferase and alkaline phosphatase, can readily be introduced by standard techniques. The presence of tags at this position does not impair the cleavage of the substrate.

A vector comprising the ST coding sequence is co-transfected into mammalian cells (e.g. COS or HeLa) with an appropriate amount of the DNA encoding the Rhomboid to be screened. The accumulation of a soluble form of the tagged N-terminal domain can then be measured in the supernatant of the cells.

Since this cleaved fragment is tagged (e.g. with GFP, luciferase or alkaline phosphatase) the detection is readily automated. Other detection methods may also be used (e.g. ELISA, western blot, radioimmunoassay etc).

This assay is performed in the presence and absence of test compounds and the cleavage efficiency is compared.

The assay may be performed using stable lines of cells which express some or all of the components (i.e. rhomboid and substrate).

As we have shown herein, rhomboid has a very high activity; reducing its concentration by ten-fold or more may actually increase its cleavage ability (as it becomes less toxic to the cell), and as low as 0.025 ng of DNA per transfection (in a 35 mm well) has been observed to give detectable activity.

An assay method employing typical amounts of input DNA (e.g. 250 ng per 35 mm well), may put the amount of Rhomboid in cells into large excess and even inhibition of >90% might be missed. Suitable concentrations of Rhomboid are rate-limiting so that the effect of inhibitors (or activators) can be detected.

This can be readily determined individually for any particular assay using routine methodology but the present data indicates that a suitable starting point for optimization would be around 0.25 ng of Rhomboid DNA transfected into the number of cells used for a 35 mm well.

Factors that might alter this level include the activity of the specific rhomboid being tested, its expression levels in the cells being used and driven by the promoter being used; the sensitivity of the detection system; and the transfection efficiency.

Function of Rhomboid

Rhomboid-1 is a Golgi-localised protein that is responsible for the proteolytic cleavage of Spitz. Moreover, since in the presence of Star and Rhomboid-1, Spitz accumulates in the Golgi apparatus, Rhomboid-dependent cleavage is the rate limiting step in the production of active Spitz and thereby EGF receptor activation.

Star and Rhomboid-1 are sufficient to cause efficient Spitz cleavage in all mammalian cell lines tested, providing indication that they are the only components required for Spitz cleavage. Since our analysis rules out the involvement of metalloproteases in Spitz processing, this further indicates that Rhomboid-1 may itself be the protease. The absence of a genetically identified candidate protease, other than Rhomboid-1, despite much genetic screening, is also consistent with this finding.

Confirmation of the protease activity of Rhomboid-1 is provided by mutagenesis analysis of conserved residues. This demonstrates that the Rhomboids are a family of novel intramembrane serine proteases, which is strongly supported by the observation that the Rhomboid-1 dependent cleavage of Spitz is sensitive to serine protease inhibitors. The four Drosophila Rhomboids tested all show distinct cleavage activities against three Drosophila EGFR ligands: Spitz, Gurken and Keren (see Table 2), indicating the specificity of their serine protease.

The Spitz TMD (i.e. residues 141-144) is sufficient to confer Rhomboid-1 sensitivity onto TGFα and the actual site of cleavage and/or recognition is within this Spitz membrane spanning domain.

Because Rhomboid is highly conserved in many species, the elucidation of the EGFR ligand signaling mechanism, as described herein finds significant application in many fields of biology and medicine.

TABLE 1

Rhomboid polypeptides

| Accession | Gene | Size | Species |
|---|---|---|---|
| P20350 | Rhomboid-1 | | Drosophila Melanogaster |
| AAK06753 | Rhomboid-3 | | Drosophila Melanogaster |
| AAK06752 | Rhomboid-2 | | Drosophila Melanogaster |
| CAA76629(XM_007948, NM_003961, AJ272344) | Rhomboid related protein (RHBL) | 438 | Homo Sapiens |
| AAK06754 | Rhomboid-4 | | Drosophila Melanogaster |
| NP_060291 | FLJ20435 | 292 | Homo Sapiens |
| T16172 | F26F4.3 | 419 | C. elegans |
| AAA02747 | AAA02747 | 325 | Saccharum hybrid cultivar H65-7052 |
| S40723 | Rhomboid homlog C489B4.2 | 397 | C. elegans |
| AAF88090 | C025417_18 | 302 | Arabidopsis thaliana |
| AAG51610 | C010795_14 | 317 | Arabidopsis thaliana |
| AAD55606 | C008016_16 | 309 | Arabidopsis thaliana |
| CAB88340 | CAB8830 | 361 | Arabidopsis thaliana |
| AAG28519 | PARL | 379 | Homo sapiens |
| AE003628 | CG5364/Rhomboid-5 | 1840 | Drosophila melanogaster |
| CAB87281 | CAB87281 | 346 | Arabidopsis thaliana |
| T36724 | T36724 | 297 | Streptomyces coelicolor |
| A55862 | AarA | 281 | Providencia stuartii |
| BAA12519 | YpgP | 507 | B. subtilis |
| AAF53172 | CG17212/Rhomboid-6 | 263 | Drosophila melanogaster |
| BAB05140 | BH1421 | 514 | Bacillus halodurans |
| T02735 | T9I4.13 | 372 | Arabidopsis thaliana |
| CAA17304 | Rv0110 | 249 | Mycobacterium tuberculosis |
| T34718 | T34718 | 383 | Streptomyces coelicolor |
| BAB21138 | BAB21138 | 393 | Oryza sativa |
| AAD36164 | E001768_13 | 222 | Thermatoga maritime |
| AAD35669 | AE001733_6 | 235 | Thermatoga maritime |
| T35521 | T33521 | 256 | Streptomyces coelicolor |
| CAC18292 | CAC18292 | 497 | Neurospora crassa |
| T05139 | F7H19.260 | 313 | Arabidopsis thaliana |
| AAG40087 | AC079374_1 | 369 | Arabidopsis thaliana |
| B75109 | PAB1920 | 212 | Pyrococcus abyssi |
| AAK04268 | AE006254_9 | 230 | Lactococcus lactis |
| CAA76716 | CAA76716 | 164 | Rattus norvegicus |
| AAF58598 | CG8972/Rhomboid-7 | 351 | Drosophila melanogaster |
| CAA86933 | CAA86933 | 276 | Acinetobacter calcoaceticus |
| CAA97104 | YGR101w/Yeast Rhomboid-1 | 346 | Saccharomyces cerevisiae |
| AAC07308 | AAC07308 | 227 | Aquifex aeolicus |
| E72574 | APE1877 | 256 | Aeropyrum pernix |
| NP_069844 | NP_069844 | 330 | Archaeoglobus fulgibus |
| AAA58222 | AAA58222 | 274 | E. coli |
| BVECGG | GlpG | 276 | E. coli |
| E71025 | PH1497 | 197 | Pyrococcus horikoshii |
| AAK03522 | GlpG | 291 | Pasteurella multocida |
| G82780 | XF0649 | 224 | Xylella fastidiosa |
| G69772 | YdcA | 199 | Bacillus subtilis |
| O14362 | C30D10.19C | 298 | Schizosaccharomyces pombe |
| F82729 | XF1054 | 232 | Xylella fastidiosa |
| BAB04236 | BH0517 | 248 | Bacillus halodurans |
| T34866 | T34866 | 285 | Streptomyces coelicolor |
| A82363 | GlpG | 277 | Vibrio cholerae |
| I64081 | GlpG | 192 | Haemophilus influenzae |
| AC026238 | AC026238 | 336 | Arabidopsis thaliana |
| AAH03653 | AAH03653 | 329 | Homo sapiens |
| D71258 | GlpG | 208 | Treponema pallidum |

TABLE 1-continued

Rhomboid polypeptides

| Accession | Gene | Size | Species |
|---|---|---|---|
| CAB9075 | CAB9075 | 223 | *Streptococcus uberis* |
| AAK24595 | AAK24595 | 218 | *Caulobacter crescentus* |
| B83259 | PA3086 | 286 | *Pseudomonas aeruginosa* |
| C82588 | XF2186 | 206 | *Xylella fastidosa* |
| AAG19304 | Vng0858c | 598 | *Halobacterium* sp.NRC-1 |
| BAB02051 | MKP6.17 | 506 | *Arabidopsis thaliana* |
| AAG18926 | Vng0361c | 333 | *Halobacterium* sp.NRC-1 |
| BAB29735 | BAB29735 | 315 | *Mus musculus* |
| E75328 | E75328 | 232 | *Deinococcus radiodurans* |
| T49293 | T16L24.70 | 269 | *Arabidopsis thaliana* |
| CAB83168 | CAB83168 | 392 | *Schizosaccharomyces pombe* |
| T45666 | F14P22.50 | 411 | *Arabidopsis thaliana* |
| P53426 | B1549_C3_240 | 251 | *Mycobacterium leprae* |
| CAC22904I | CAC22904I | 214 | *Sulfolobus solfataricus* |
| T41608 | SPCC790.03 | 248 | *Schizosaccharomyces pombe* |
| H81375 | Cj1003c | 172 | *Campylobacter jejuni* |
| CAC31552 | CAC31552 | 238 | *Mycobacterium leprae* |
| Q10647 | YD37_MYCTU | 240 | *Mycobacterium tuberculosis* |
| NP_015078 | Ypl246cp | 262 | *Saccharomyces cerevisae* |
| S76748 | S76748 | 198 | *Synechocystis* sp. |
| NM_017821 | RHBDL2 | | *Homo sapiens* |
| BE778475 | RHBDL3 (partial) | | *Homo sapiens* |

TABLE 2

| Accession | Name | Size | Species |
|---|---|---|---|
| Q01083 [SEQ ID NO: 39] | Spitz | 234 | *D. melanogaster* |
| AAF63381 [SEQ ID NO: 40] | Keren/Gritz/Spitz-2 | 217 | *D. melanogaster* |
| P42287 [SEQ ID NO: 41] | Gurken | 294 | *D. melanogaster* |
| P01135 [SEQ ID NO: 42] | TGF-α | 160 | *Homo sapiens* |
| P00533 [SEQ ID NO: 43] | EGF | 1210 | *Homo sapiens* |
| Q99075 [SEQ ID NO: 44] | HB-EGF | 208 | *Homo sapiens* |
| JC1467 [SEQ ID NO: 45] | Betacellulin | 178 | *Homo sapiens* |
| A34702 [SEQ ID NO: 46] | Amphiregulin | 252 | *Homo sapiens* |
| BAA22146 [SEQ ID NO: 47] | Epiregulin | 169 | *Homo sapiens* |
| Q03345 [SEQ ID NO: 48] | Lin-3 | 438 | *C. elegans* |

TABLE 3

| Name | WT Rho-1 sequences present in construct |
|---|---|
| N1 | 1-101 |
| N2 | 1-122 |
| N3 | 1-135 |
| N4 | 1-164 |
| N5 | 1-210 |
| N6 | 1-236 |
| N7 | 1-299 |
| N8 | 1-328 |
| C5 | 208-355 |
| C4 | 162-355 |
| C3 | 151-355 |
| C2 | 136-355 |
| C1 | 120-355 |

The invention claimed is:

1. A method for identifying a modulator of the protease activity of a Rhomboid polypeptide, which method comprises:
   (a) bringing into contact a Rhomboid polypeptide and a polypeptide substrate in the presence of a test compound; and
   (b) determining the protease activity of the Rhomboid polypeptide, wherein said protease activity is determined by determining proteolytic cleavage of the polypeptide substrate by the Rhomboid polypeptide,
   wherein a difference between the protease activity of the Rhomboid polypeptide in the presence of the test compound and in the absence of the test compound is indicative that the test compound modulates the protease activity of the Rhomboid polypeptide.

2. A method according to claim 1 wherein the Rhomboid polypeptide is Human Rhomboid-2 (RHBDL-2).

3. A method according to claim 1 wherein the Rhomboid polypeptide is selected from the group consisting of Drosophila Rhomboid 1 Drosophila Rhomboid 2, Drosophila Rhomboid 3, Drosophila Rhomboid 4, Human RHBDL-3, Human RHBDL-2 and Human RHBDL-3, E, coli glgG, B. subtilis ypqP, P. 15 stuartii A55862 gene product, P. aeruginosa B83259 gene product, S. cervisiae YGR101w and S. cervisiae YPL246c.

4. A method according to claim 1 wherein the Rhomboid polypeptide comprises an ER (endoplasmic reticulum) retention signal.

5. A method according to claim 1 wherein the polypeptide substrate is an EGFR ligand.

6. A method according to claim 5 wherein the polypeptide substrate is human EGF (P00533).

7. A method according to claim 1 wherein the polypeptide substrate comprises a detectable label.

8. A method according to claim 1 comprising identifying said test compound as a modulator of Rhomboid protease activity.

9. A method according to claim 8 comprising isolating said test compound.

10. A method according to claim 9 comprising formulating said test compound in a pharmaceutical composition with a pharmaceutically acceptable excipient, vehicle or carrier.

11. A method according to claim 1 wherein the wherein the Rhomboid polypeptide is selected from the group consisting of Drosophila Melanogaster Rhomboid-1; Drosophila Melanogaster Rhomboid-3; Drosophila Melanogaster Rhomboid-2; Homo Sapiens Rhomboid related protein (RHBL); Drosophila Melanogaster Rhomboid-4; Homo Sapiens FLJ20435; C. elegans F26F4.3; Saccharum hybrid cultivar H65-7052 AAA02747; C. elegans Rhomboid homlog C489B4.2; Arabidopsis thaliana C025417$_{13}$ 18; Arabidopsis thaliana C0010795$_{13}$14; Arabidopsis thaliana C008016$_{13}$16; Arabidopsis thaliana CAB8830; Homo sapiens PARL; Drosophila melanogaster CG5364/Rhomboid-5; Arabidopsis thaliana CAB87281; Streptomyces coelicolor T36724; Providencia stuartii AarA; B. subtilis YpgP; Drosophila melanogaster CG17212/Rhomboid-6; Bacillus halodurans BH1421; Arabidopsis thaliana T914.13; Mycobacterium tuberculosis Rv0110; Streptomyces coelicolor T34718; Oryza sativa BAB21138; Thermatoga maritime E001768$_{13}$13 Thermatoga maritime AE001733$_{13}$6 Streptomyces coelicolor T33521; Neurospora crassa CAC18292; Arabidopsis thaliana F7H19.260; Arabidopsis thaliana AC079374$_{13}$1; Pyrococcus abyssi PAB 1920; Lactococcus lactis AE006254$_{13}$9; Rattus norvegicus CAA76716; Drosophila melanogaster CG8972/Rhomboid-7; Acinetobacter calcoaceticus CAA86933; Saccharomyces cerevisiae YGR101w/Yeast Rhomboid-1; Aquifex aeolicus AAC07308; Aeropyrum pernix APEI1877; Archaeoglobus fulgibus NP$_{13}$069844; E. coli AAA58222; E. coli GlpG; Pyrococcus horikoshii PH1497; Pasteurella multocida GlpG; Xylella fastidiosa XF0649; Bacillus subtilis YdcA; Schizosaccharomyces pombe C30D10.19C; Xylella fastidiosa XF1054; Bacillus halodurans BH0517; Streptomyces coelicolor T34866; Vibrio cholerae GlpG; Haemophilus influenzae GlpG; Arabidopsis thaliana AC026238; Homo sapiens AAH03653; Treponema pallidum GlpG; Streptococcus uberis CAB9075; Caulobacter crescentus AAK24595; Pseudomonas aeruginosa PA3086; Xylella fastidosa XF2186; Halobacterium sp. NRC-1 Vng0858c; Arabidopsis thaliana MKP6.17; Halobacterium sp.NRC-1 Vng0361c; Mus musculus BAB29735; Deinococcus radiodurans E75328; Arabidopsis thaliana T16L24.70; Schizosaccharomyces pombe CAB83168; Arabidopsis thaliana F14P22.50; Mycobacterium leprae B1549$_{13}$C3$_{13}$240; Sulfolobus solfataricus CAC22904l; Schizosaccharomyces pombe SPCC790.03; Campylobacter jejuni Cj 1003c; Mycobacterium leprae CAC31552; Mycobacterium tuberculosis YD37$_{13}$MYCTU; Saccharomyces cerevisae Ypl246cp; Synechocystis sp. S76748; Homo sapiens RHBDL2; and Homo sapiens RHBDL3.

12. A method according to claim 5 wherein the polypeptide substrate is selected from the group consisting of D. melanogaster Spitz; D. melanogaster Keren/Gritz/Spitz-2; D. melanogaster Gurken; Homo sapiens TGF-α; Homo sapiens EGF; Homo sapiens HB-EGF Homo sapiens Betacellulin; Homo sapiens Amphiregulin; Homo sapiens Epiregulin and C. elegans Lin-3.

* * * * *

SEQUENCE LISTING

```
<160> NUMBER OF SEQ ID NOS: 48

<210> SEQ ID NO 1
<211> LENGTH: 5
<212> TYPE: PRT
<213> ORGANISM: Drosophila melanogaster

<400> SEQUENCE: 1

Ile Ala Ser Gly Ala
 1               5

<210> SEQ ID NO 2
<211> LENGTH: 7
```

```
<212> TYPE: PRT
<213> ORGANISM: Drosophila melanogaster

<400> SEQUENCE: 2

Ala Ser Ile Ala Ser Gly Ala
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: synthetic
      motif
<220> FEATURE:
<221> NAME/KEY: SITE
<222> LOCATION: (2)
<223> OTHER INFORMATION: Xaa may be any amino acid residue

<400> SEQUENCE: 3

Gly Xaa Ser Gly
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: synthetic
     motif

<400> SEQUENCE: 4

Gly Ala Ser Gly
 1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: ER
      retention signal sequence

<400> SEQUENCE: 5

Lys Asp Glu Leu
 1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Conserved
      serine protease motif

<400> SEQUENCE: 6

Gly Ala Ser Gly Gly
 1               5

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Antisense
      oligonucleotide

<400> SEQUENCE: 7
```
tcttgctctt cggtgtcatt atcgc 25

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: synthetic
      motif
<220> FEATURE:
<221> NAME/KEY: SITE
<222> LOCATION: (2)
<223> OTHER INFORMATION: Xaa may be any amino acid residue

<400> SEQUENCE: 8

Gly Xaa Ser Gly Gly
 1               5

<210> SEQ ID NO 9
<211> LENGTH: 5
<212> TYPE: PRT
<213> ORGANISM: Homo sapiens

<400> SEQUENCE: 9

Ile Thr Ala Leu Val
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ala Gly Gly
 1

<210> SEQ ID NO 11
<211> LENGTH: 438
<212> TYPE: PRT
<213> ORGANISM: Homo sapiens

<400> SEQUENCE: 11

Met Gly Arg Val Glu Asp Gly Gly Thr Thr Glu Glu Leu Glu Asp Trp
 1               5                  10                  15

Asp Pro Gly Thr Ser Ala Leu Pro Ala Pro Gly Ile Lys Gln Gly Pro
                20                  25                  30

Arg Glu Gln Thr Gly Thr Gly Pro Leu Ser Gln Lys Cys Trp Glu Pro
            35                  40                  45

Glu Pro Asp Ala Pro Ser Gln Pro Gly Pro Ala Leu Trp Ser Arg Gly
        50                  55                  60

Arg Ala Arg Thr Gln Ala Leu Ala Gly Gly Ser Ser Leu Gln Gln Leu
    65                  70                  75                  80

Asp Pro Glu Asn Thr Gly Phe Ile Gly Ala Asp Thr Phe Thr Gly Leu
                85                  90                  95

Val His Ser His Glu Leu Pro Leu Asp Pro Ala Lys Leu Asp Met Leu
            100                 105                 110

Val Ala Leu Ala Gln Ser Asn Glu Gln Gly Gln Val Cys Tyr Gln Glu
        115                 120                 125

Leu Val Asp Leu Ile Ser Ser Lys Arg Ser Ser Phe Lys Arg Ala
    130                 135                 140

```
Ile Ala Asn Gly Gln Arg Ala Leu Pro Arg Asp Gly Pro Leu Asp Glu
145                 150                 155                 160

Pro Gly Leu Gly Val Tyr Lys Arg Phe Val Arg Tyr Val Ala Tyr Glu
            165                 170                 175

Ile Leu Pro Cys Glu Val Asp Arg Arg Trp Tyr Phe Tyr Arg His Arg
        180                 185                 190

Ser Cys Pro Pro Pro Val Phe Met Ala Ser Val Thr Leu Ala Gln Ile
            195                 200                 205

Ile Val Phe Leu Cys Tyr Gly Ala Arg Leu Asn Lys Trp Val Leu Gln
        210                 215                 220

Thr Tyr His Pro Glu Tyr Met Lys Ser Pro Leu Val Tyr His Pro Gly
225                 230                 235                 240

His Arg Ala Arg Ala Trp Arg Phe Leu Thr Tyr Met Phe Met His Val
            245                 250                 255

Gly Leu Glu Gln Leu Gly Phe Asn Ala Leu Leu Gln Leu Met Ile Gly
            260                 265                 270

Val Pro Leu Glu Met Val His Gly Leu Leu Arg Ile Ser Leu Leu Tyr
        275                 280                 285

Leu Ala Gly Val Leu Ala Gly Ser Leu Thr Val Ser Ile Thr Asp Met
290                 295                 300

Arg Ala Pro Val Val Gly Gly Ser Gly Gly Val Tyr Ala Leu Cys Ser
305                 310                 315                 320

Ala His Leu Ala Asn Val Val Met Asn Trp Ala Gly Met Arg Cys Pro
            325                 330                 335

Tyr Lys Leu Leu Arg Met Val Leu Ala Leu Val Cys Met Ser Ser Glu
            340                 345                 350

Val Gly Arg Ala Val Trp Leu Arg Phe Ser Pro Pro Leu Pro Ala Ser
            355                 360                 365

Gly Pro Gln Pro Ser Phe Met Ala His Leu Ala Gly Ala Val Val Gly
            370                 375                 380

Val Ser Met Gly Leu Thr Ile Leu Arg Ser Tyr Glu Glu Arg Leu Arg
385                 390                 395                 400

Asp Gln Cys Gly Trp Trp Val Val Leu Leu Ala Tyr Gly Thr Phe Leu
            405                 410                 415

Leu Phe Ala Val Phe Trp Asn Val Phe Ala Tyr Asp Leu Leu Gly Ala
            420                 425                 430

His Ile Pro Pro Pro
            435

<210> SEQ ID NO 12
<211> LENGTH: 292
<212> TYPE: PRT
<213> ORGANISM: Homo sapiens

<400> SEQUENCE: 12

Met Asn Leu Asn Met Gly Arg Glu Met Lys Glu Glu Leu Glu Glu Glu
1               5                   10                  15

Glu Lys Met Arg Glu Asp Gly Gly Lys Asp Arg Ala Lys Ser Lys
            20                  25                  30

Lys Val His Arg Ile Val Ser Lys Trp Met Leu Pro Glu Lys Ser Arg
            35                  40                  45

Gly Thr Tyr Leu Glu Arg Ala Asn Cys Phe Pro Pro Val Phe Ile
        50                  55                  60

Ile Ser Ile Ser Leu Ala Glu Leu Ala Val Phe Ile Tyr Tyr Ala Val
```

```
            65                  70                  75                  80
Trp Lys Pro Gln Lys Gln Trp Ile Thr Leu Asp Thr Gly Ile Leu Glu
                        85                  90                  95

Ser Pro Phe Ile Tyr Ser Pro Glu Lys Arg Glu Glu Ala Trp Arg Phe
                100                 105                 110

Ile Ser Tyr Met Leu Val His Ala Gly Val Gln His Ile Leu Gly Asn
            115                 120                 125

Leu Cys Met Gln Leu Val Leu Gly Ile Pro Leu Glu Met Val His Lys
        130                 135                 140

Gly Leu Arg Val Gly Leu Val Tyr Leu Ala Gly Val Ile Ala Gly Ser
145                 150                 155                 160

Leu Ala Ser Ser Ile Phe Asp Pro Leu Arg Tyr Leu Val Gly Ala Ser
                165                 170                 175

Gly Gly Val Tyr Ala Leu Met Gly Gly Tyr Phe Met Asn Val Leu Val
                180                 185                 190

Asn Phe Gln Glu Met Ile Pro Ala Phe Gly Ile Phe Arg Leu Leu Ile
            195                 200                 205

Ile Ile Leu Ile Ile Val Leu Asp Met Gly Phe Ala Leu Tyr Arg Arg
        210                 215                 220

Phe Phe Val Pro Glu Asp Gly Ser Pro Val Ser Phe Ala Ala His Ile
225                 230                 235                 240

Ala Gly Gly Phe Ala Gly Met Ser Ile Gly Tyr Thr Val Phe Ser Cys
                245                 250                 255

Phe Asp Lys Ala Leu Leu Lys Asp Pro Arg Phe Trp Ile Ala Ile Ala
            260                 265                 270

Ala Tyr Leu Ala Cys Val Leu Phe Ala Val Phe Phe Asn Ile Phe Leu
        275                 280                 285

Ser Pro Ala Asn
        290

<210> SEQ ID NO 13
<211> LENGTH: 355
<212> TYPE: PRT
<213> ORGANISM: Drosophila melanogaster

<400> SEQUENCE: 13

Met Glu Asn Pro Thr Gln Asn Val Asn Glu Thr Lys Val Asp Leu Gly
  1               5                  10                  15

Gln Glu Lys Glu Lys Glu Ala Ser Gln Glu Glu Glu His Ala Thr Ala
                20                  25                  30

Ala Lys Glu Thr Ile Ile Asp Ile Pro Ala Ala Cys Ser Ser Ser Ser
            35                  40                  45

Asn Ser Ser Ser Tyr Asp Thr Asp Cys Ser Thr Ala Ser Ser Thr Cys
        50                  55                  60

Cys Thr Arg Gln Gly Glu His Ile Tyr Met Gln Arg Glu Ala Ile Pro
65                  70                  75                  80

Ala Thr Pro Leu Pro Glu Ser Glu Asp Ile Gly Leu Leu Lys Tyr Val
                85                  90                  95

His Arg Gln His Trp Pro Trp Phe Ile Leu Val Ile Ser Ile Ile Glu
            100                 105                 110

Ile Ala Ile Phe Ala Tyr Asp Arg Tyr Thr Met Pro Ala Gln Asn Phe
        115                 120                 125

Gly Leu Pro Val Pro Ile Pro Ser Asp Ser Val Leu Val Tyr Arg Pro
    130                 135                 140
```

-continued

```
Asp Arg Arg Leu Gln Val Trp Arg Phe Phe Ser Tyr Met Phe Leu His
145                 150                 155                 160
Ala Asn Trp Phe His Leu Gly Phe Asn Ile Val Ile Gln Leu Phe Phe
                165                 170                 175
Gly Ile Pro Leu Glu Val Met His Gly Thr Ala Arg Ile Gly Val Ile
            180                 185                 190
Tyr Met Ala Gly Val Phe Ala Gly Ser Leu Gly Thr Ser Val Val Asp
        195                 200                 205
Ser Glu Val Phe Leu Val Gly Ala Ser Gly Gly Val Tyr Ala Leu Leu
    210                 215                 220
Ala Ala His Leu Ala Asn Ile Thr Leu Asn Tyr Ala His Met Lys Ser
225                 230                 235                 240
Ala Ser Thr Gln Leu Gly Ser Val Val Ile Phe Val Ser Cys Asp Leu
                245                 250                 255
Gly Tyr Ala Leu Tyr Thr Gln Tyr Phe Asp Gly Ser Ala Phe Ala Lys
            260                 265                 270
Gly Pro Gln Val Ser Tyr Ile Ala His Leu Thr Gly Ala Leu Ala Gly
        275                 280                 285
Leu Thr Ile Gly Phe Leu Val Leu Lys Asn Phe Gly His Arg Glu Tyr
    290                 295                 300
Glu Gln Leu Ile Trp Trp Leu Ala Leu Gly Val Tyr Cys Ala Phe Thr
305                 310                 315                 320
Val Phe Ala Ile Val Phe Asn Leu Ile Asn Thr Val Thr Ala Gln Leu
                325                 330                 335
Met Glu Glu Gln Gly Glu Val Ile Thr Gln His Leu Leu His Asp Leu
            340                 345                 350
Gly Val Ser
        355
```

<210> SEQ ID NO 14
<211> LENGTH: 1320
<212> TYPE: DNA
<213> ORGANISM: Homo sapiens

<400> SEQUENCE: 14

```
atgggcgagc accccagccc gggccccgcg gtggccgcct cgccgaggc ggagcgcatc      60
gaggagctgg aacccgaggc cgaggagcgg ctgcccgcgg cgccggagga cggtggggag     120
atggaagtga aaccaggccc ccaacccaca caacgaaagc gggaaagtct gaatgggtt     180
gggggggctgg ggaaggagcc ccagatggca gcaatacaaa gagagaatct gtttgaccct     240
gggaacacag gctacattag cacaggcaag ttccggagtc ttctggagag ccacagctcc     300
aagctggacc cgcacaaaag ggaggtcctc ctggctcttg ccgacagcca cgcggatggg     360
cagatcggct accaggattt tgtcagccta atgagcaaca agcgttccaa cagcttccgc     420
caagccatcc tgcagggcaa ccgcaggcta agcagcaagg ccctgctgga ggcgaagggg     480
ctgagcctct cgcagcgact tatccgccat gtggcctatg agaccctgcc ccgggaaatt     540
gaccgcaagt ggtactatga cagctacacc tgctgccccc caccctggtt catgatcaca     600
gtcacgctgc tggaggcaag gacaaggtg gccttttttcc tctacaatgg ggtgtcacta     660
ggtcaatttg tactgcaggt aactcatcca cgttacttga agaactccct ggtttaccac     720
ccacagctgc gagcacaggt ttggcgctac ctgacataca tcttcatgca tgcagggata     780
gaacacctgg gactcaatgt ggtgctgcag ctgctggtgg gggtgccct ggagatggtg     840
catggagcca cccgaattgg gcttgtctac gtggccggtg ttgtggcagg ttccttggca     900
```

```
gtgtctgtgg ctgacatgac cgctccagtc gtgggctctt ctggagggt  gtatgctctc      960 gtctctgccc atctggccaa cattgtcatg aactggtcag gcatgaagtg ccagttcaag     1020
ctgctgcgga tggctgtggc ccttatctgt gtgagcatgg agtttgggcg ggccgtgtgg     1080
ctccgcttcc acccgtcggc ctatcccccg tgccctcacc caagctttgt ggcgcacttg     1140
ggtggcgtgg ccgtgggcat caccctgggc gtggtggtcc tgaggaacta cgagcagagg     1200
ctccaggacc agtcactgtg gtggattttt gtggccatgt acaccgtctt cgtgctgttc     1260
gctgtcttct ggaacatctt tgcctacacc ctgctggact aaagctgcc  gcctccccc      1320

<210> SEQ ID NO 15
<211> LENGTH: 439
<212> TYPE: PRT
<213> ORGANISM: Homo sapiens

<400> SEQUENCE: 15

Met Gly Glu His Pro Ser Pro Gly Pro Ala Val Ala Ala Cys Ala Glu
  1               5                  10                  15

Ala Glu Arg Ile Glu Glu Leu Glu Pro Glu Ala Glu Glu Arg Leu Pro
             20                  25                  30

Ala Ala Pro Glu Asp Gly Gly Glu Met Glu Val Lys Pro Gly Pro Gln
         35                  40                  45

Pro Thr Gln Arg Lys Arg Glu Ser Leu Asn Gly Val Gly Gly Leu Gly
     50                  55                  60

Lys Glu Pro Gln Met Ala Ala Ile Gln Arg Glu Asn Leu Phe Asp Pro
 65                  70                  75                  80

Gly Asn Thr Gly Tyr Ile Ser Thr Gly Lys Phe Arg Ser Leu Leu Glu
                 85                  90                  95

Ser His Ser Ser Lys Leu Asp Pro His Lys Arg Glu Val Leu Leu Ala
            100                 105                 110

Leu Ala Asp Ser His Ala Asp Gly Gln Ile Gly Tyr Gln Asp Phe Val
        115                 120                 125

Ser Leu Met Ser Asn Lys Arg Ser Asn Ser Phe Arg Gln Ala Ile Leu
    130                 135                 140

Gln Gly Asn Arg Arg Leu Ser Ser Lys Ala Leu Leu Glu Glu Lys Gly
145                 150                 155                 160

Leu Ser Leu Ser Gln Arg Leu Ile Arg His Val Ala Tyr Glu Thr Leu
                165                 170                 175

Pro Arg Glu Ile Asp Arg Lys Trp Tyr Tyr Asp Ser Tyr Thr Cys Cys
            180                 185                 190

Pro Pro Pro Trp Phe Met Ile Thr Val Thr Leu Leu Glu Ala Arg Thr
        195                 200                 205

Arg Val Ala Phe Phe Leu Tyr Asn Gly Val Ser Leu Gly Gln Phe Val
    210                 215                 220

Leu Gln Val Thr His Pro Arg Tyr Leu Lys Asn Ser Leu Val Tyr His
225                 230                 235                 240

Pro Gln Leu Arg Ala Gln Val Trp Arg Tyr Leu Thr Tyr Ile Phe Met
                245                 250                 255

His Ala Gly Ile Glu His Leu Gly Leu Asn Val Val Leu Gln Leu Leu
            260                 265                 270

Val Gly Val Pro Leu Glu Met Val His Gly Ala Thr Arg Ile Gly Leu
        275                 280                 285

Val Tyr Val Ala Gly Val Ala Gly Ser Leu Ala Val Ser Val Ala
    290                 295                 300
```

```
Asp Met Thr Ala Pro Val Val Gly Ser Ser Gly Val Tyr Ala Leu
305                 310                 315                 320

Val Ser Ala His Leu Ala Asn Ile Val Met Asn Trp Ser Gly Met Lys
                325                 330                 335

Cys Gln Phe Lys Leu Leu Arg Met Ala Val Ala Leu Ile Cys Met Ser
                340                 345                 350

Met Glu Phe Gly Arg Ala Val Trp Leu Arg Phe His Pro Ser Ala Tyr
                355                 360                 365

Pro Pro Cys Pro His Pro Ser Phe Val Ala His Leu Gly Gly Val Ala
        370                 375                 380

Val Gly Ile Thr Leu Gly Val Leu Arg Asn Tyr Glu Gln Arg Leu
385                 390                 395                 400

Gln Asp Gln Ser Leu Trp Trp Ile Phe Val Ala Met Tyr Thr Val Phe
                405                 410                 415

Val Leu Phe Ala Val Phe Trp Asn Ile Phe Ala Tyr Thr Leu Leu Asp
                420                 425                 430

Leu Lys Leu Pro Pro Pro Pro
        435

<210> SEQ ID NO 16
<211> LENGTH: 2259
<212> TYPE: DNA
<213> ORGANISM: Danio rerio

<400> SEQUENCE: 16
```

| | | | | | |
|---|---|---|---|---|---|
| cactgttggc | ctactgggat | gccccgctaa | caaattcatg | aatgggagtg | aagcaacgct | 60
| actgacgcag | atagagaaat | gggcgataat | gacaccgaag | agcaagactc | tttgcagaag | 120
| aaggacgaag | aagctggtaa | ccgagacaat | ccggtcagaa | gagttcggag | ggtcgagaag | 180
| tttcataaga | atgtttctaa | atggatgctt | cccgaggagt | tacatgagac | ttatcttgag | 240
| cgggcgaact | gctgtccgcc | accgatcttc | atcatcctca | tcagtttagc | agagctggcc | 300
| gtgtttatct | actacgctgt | atggaagcct | caaaaacagt | ggataactct | aggaactggg | 360
| atctgggata | gtcctcttac | ctataggcca | gaacaacgca | aggaggcttg | gcgctttgtt | 420
| tcctacatgt | ttgtacatgc | cggggtggag | catatcatgg | ggaacctatt | aatgcagctt | 480
| cttctgggta | ttcctctgga | actggtccat | aaaggctttg | aagttggcat | ggtgtacatg | 540
| tgtgggtcc | tcgcagggtc | tctggccagc | tccatctttg | atcctttcag | tgctcttgtg | 600
| ggagcttcag | gtggtgttta | tgcccttatg | ggtggctact | tcatgaatgc | cattgtgaat | 660
| ttccgggaga | tgagagttct | tctaggagtg | tttcgcatct | tagtgattgt | tttgattgtt | 720
| ggaacagatg | ttggatttgc | tctttataga | aggttcattg | tccacgaggc | tggcctaaag | 780
| gtctcttttg | tggctcatat | tggcggtggc | atagcaggca | tgaccattgg | ttatgtgttt | 840
| ttcaccaact | acaataaaga | gcttctaaaa | gacccacgct | tctggatgtg | cattgtggga | 900
| tacatcgtct | tcttactgtt | tgcagtcatt | tcaacatct | tcttgtcccc | agcacccgca | 960
| tgaggtcatc | aatggacagt | cgaaccttt | ttttattta | taaagaatg | aggtcaacac | 1020
| aactgtcaga | caatcctgtt | ggtatttata | gactcataaa | gggttagttc | aactgaaaac | 1080
| tctgtattga | cccatattgt | tctttcagaa | gttcatcttt | gaaacacaaa | tgaagatatt | 1140
| tttaaatcaa | gccgagcgat | ttcgtttctt | ctattcagag | tctgtttacc | ctacaccttt | 1200
| gactatgaaa | ggatcagaat | ccatataaat | aggttcacat | tttatgaatg | aatagattta | 1260
| attttggttt | acatttcaga | aatttggatt | tggaaatctt | tagggtttca | ttaaaagtat | 1320

```
cctaatttgt gtattgaaga tgggaagatt tcttatgggt ttggaatggg atgagggagt    1380
ctatttacat tttacactga actaacccct taggaaatat gctaacacac tacaagcaca    1440
tctaaagaaa gtaactgtca tatttggat attttttaaa tgtaattttt tttaatgtca     1500
tgtaatttat gttttttgtt tagttttgta ttgttttgct taacacatgt acttaagtaa    1560
tgtattgcct caggggaaaa aatgataaag catatatttt ttaattgttt gggttttaca    1620
aaatcattgg gcatttctgg actggccaac atttttaatt catgactaaa cagcttggtt    1680
tatttgaatt cagttcaatt tgtttggaga taaatgcatt taaagttcac caaaaaatat    1740
aaattctatc atcatatata tacccttttac ttgtaacaaa cctttcattc ttctgttaaa   1800
cacaaaacaa gatattgtga agaattttga aaaccagtaa ccatcgactt tcaaagtaca    1860
acattcttta aaacatcttc attcgtgttt tagagaacgt ttttgtactt aaaagaaact    1920
cataaatttt agaaaaccct tgagggtgag gaatttgtga gtaaattttg atttgagggt    1980
taactatccc tttaaaaaaa gaggtttcgt tttgatacca atagagggca gcattgatca    2040
gcatgtgggc attggaagac actgacctat aaaaagtagg aaattgttaa atcagtgcta    2100
atgacatgca tctgtattta ccctacgtat ttgtccctaa ttatcaaatc atttattttc    2160
agaaatgggt ttgggtttgg aatgttttgg ccatatagag gccatatagc cttttttatt    2220 tttttttatga aataataaaa agaattgtgc caatgtttt                          2259
```

<210> SEQ ID NO 17
<211> LENGTH: 294
<212> TYPE: PRT
<213> ORGANISM: Danio rerio

<400> SEQUENCE: 17

```
Met Gly Asp Asn Asp Thr Glu Glu Gln Asp Ser Leu Gln Lys Lys Asp
 1               5                  10                  15

Glu Glu Ala Gly Asn Arg Asp Asn Pro Val Arg Val Arg Arg Val
            20                  25                  30

Glu Lys Phe His Lys Asn Val Ser Lys Trp Met Leu Pro Glu Glu Leu
        35                  40                  45

His Glu Thr Tyr Leu Glu Arg Ala Asn Cys Cys Pro Pro Ile Phe
    50                  55                  60

Ile Ile Leu Ile Ser Leu Ala Glu Leu Ala Val Phe Ile Tyr Tyr Ala
 65                 70                  75                  80

Val Trp Lys Pro Gln Lys Gln Trp Ile Thr Leu Gly Thr Gly Ile Trp
                85                  90                  95

Asp Ser Pro Leu Thr Tyr Arg Pro Glu Gln Arg Lys Glu Ala Trp Arg
            100                 105                 110

Phe Val Ser Tyr Met Phe Val His Ala Gly Val Glu His Ile Met Gly
        115                 120                 125

Asn Leu Leu Met Gln Leu Leu Leu Gly Ile Pro Leu Glu Leu Val His
    130                 135                 140

Lys Gly Phe Glu Val Gly Met Val Tyr Met Cys Gly Val Leu Ala Gly
145                 150                 155                 160

Ser Leu Ala Ser Ser Ile Phe Asp Pro Phe Ser Ala Leu Val Gly Ala
                165                 170                 175

Ser Gly Gly Val Tyr Ala Leu Met Gly Gly Tyr Phe Met Asn Ala Ile
            180                 185                 190

Val Asn Phe Arg Glu Met Arg Val Leu Leu Gly Val Phe Arg Ile Leu
        195                 200                 205
```

-continued

```
Val Ile Val Leu Ile Val Gly Thr Asp Val Gly Phe Ala Leu Tyr Arg
    210                 215                 220

Arg Phe Ile Val His Glu Ala Gly Leu Lys Val Ser Phe Val Ala His
225                 230                 235                 240

Ile Gly Gly Gly Ile Ala Gly Met Thr Ile Gly Tyr Val Phe Phe Thr
                245                 250                 255

Asn Tyr Asn Lys Glu Leu Leu Lys Asp Pro Arg Phe Trp Met Cys Ile
            260                 265                 270

Val Gly Tyr Ile Val Phe Leu Leu Phe Ala Val Ile Phe Asn Ile Phe
        275                 280                 285

Leu Ser Pro Ala Pro Ala
    290

<210> SEQ ID NO 18
<211> LENGTH: 9
<212> TYPE: PRT
<213> ORGANISM: Drosophila melanogaster

<400> SEQUENCE: 18

Lys Ala Ser Ile Ala Ser Gly Ala Met
  1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 19

Gln Ala Ser Ile Ala Ser Gly Ala Met
  1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 20

Lys Phe Ser Ile Ala Ser Gly Ala Met
  1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 21

Lys Ala Phe Ile Ala Ser Gly Ala Met
  1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Mutated
```

```
                Spitz sequence

<400> SEQUENCE: 22

Lys Ala Ser Phe Ala Ser Gly Ala Met
  1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 23

Lys Ala Ser Ile Phe Ser Gly Ala Met
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 24

Lys Ala Ser Ile Ala Phe Gly Ala Met
  1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 25

Lys Ala Ser Ile Ala Ser Phe Ala Met
  1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 26

Lys Ala Ser Ile Ala Ser Gly Phe Met
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 27

Lys Ala Ser Ile Ala Ser Gly Ala Phe
  1               5

<210> SEQ ID NO 28
```

-continued

```
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 28

Lys Tyr Ser Ile Ala Ser Gly Ala Met
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 29

Lys Ala Ser Gly Ala Ser Gly Ala Met
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 30

Lys Ala Ser Ile Thr Ser Gly Ala Met
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 31

Lys Ala Ser Ile Ala Ala Gly Ala Met
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 32

Lys Ala Ser Ile Ala Ser Leu Ala Met
  1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 33
```

-continued

Lys Ala Ser Ile Ala Ser Gly Val Met
  1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 34

Lys Ala Ala Ile Ala Ser Gly Ala Met
  1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 35

Lys Val Ser Ile Ala Ser Gly Ala Met
  1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 36

Lys Ala Ser Ile Ala Ser Pro Ala Met
  1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 37

Lys Ala Ser Ile Ala Ser Gly Gly Met
  1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Mutated
      Spitz sequence

<400> SEQUENCE: 38

Lys Ala Ser Ile Ala Ser Ile Ala Met
  1               5

<210> SEQ ID NO 39
<211> LENGTH: 234
<212> TYPE: PRT
<213> ORGANISM: D. melanogaster

```
<400> SEQUENCE: 39

Met His Ser Thr Met Ser Val Gln His Gly Leu Val Ala Leu Val Leu
 1               5                  10                  15

Ile Gly Cys Leu Ala His Pro Trp His Val Glu Ala Cys Ser Ser Arg
             20                  25                  30

Thr Val Pro Lys Pro Arg Ser Ser Ile Ser Ser Met Ser Gly Thr
         35                  40                  45

Ala Leu Pro Pro Thr Gln Ala Pro Val Thr Ser Ser Thr Thr Met Arg
     50                  55                  60

Thr Thr Thr Thr Thr Thr Pro Arg Pro Asn Ile Thr Phe Pro Thr Tyr
 65                  70                  75                  80

Lys Cys Pro Glu Thr Phe Asp Ala Trp Tyr Cys Leu Asn Asp Ala His
                 85                  90                  95

Cys Phe Ala Val Lys Ile Ala Asp Leu Pro Val Tyr Ser Cys Glu Cys
                100                 105                 110

Ala Ile Gly Phe Met Gly Gln Arg Cys Glu Tyr Lys Glu Ile Asp Asn
            115                 120                 125

Thr Tyr Leu Pro Lys Arg Pro Arg Pro Met Leu Glu Lys Ala Ser Ile
130                 135                 140

Ala Ser Gly Ala Met Cys Ala Leu Val Phe Met Leu Phe Val Cys Leu
145                 150                 155                 160

Ala Phe Tyr Leu Arg Phe Glu Gln Arg Ala Ala Lys Lys Ala Tyr Glu
                165                 170                 175

Leu Glu Gln Glu Leu Gln Gln Gly Tyr Asp Asp Asp Gly Gln Cys
            180                 185                 190

Glu Cys Cys Arg Asn Arg Cys Cys Pro Asp Gly Gln Glu Pro Val Ile
            195                 200                 205

Leu Glu Arg Lys Leu Pro Tyr His Met Arg Leu Glu His Ala Leu Met
210                 215                 220

Ser Phe Ala Ile Arg Arg Ser Asn Lys Leu
225                 230

<210> SEQ ID NO 40
<211> LENGTH: 217
<212> TYPE: PRT
<213> ORGANISM: D. melanogaster

<400> SEQUENCE: 40

Met Arg Ala Gln Asp Leu Leu Leu Ala Thr Ala Leu Ile Gly Ala
 1               5                  10                  15

Tyr Leu Pro Leu Thr Ala Ala Cys Ser Ser Arg Ala Ile Ala Lys Pro
             20                  25                  30

Arg Pro Thr Ala Ala Pro Ile Leu Pro Pro Asp Asn Val Glu Ile Ser
         35                  40                  45

Thr Thr Pro Arg Pro Asn Val Thr Phe Pro Ile Phe Ala Cys Pro Pro
     50                  55                  60

Thr Tyr Val Ala Trp Tyr Cys Leu Asn Asp Gly Thr Cys Phe Thr Val
 65                  70                  75                  80

Lys Ile His Asn Glu Ile Leu Tyr Asn Cys Glu Cys Ala Leu Gly Phe
                 85                  90                  95

Met Gly Pro Arg Cys Glu Tyr Lys Glu Ile Asp Gly Ser Tyr Leu Pro
                100                 105                 110

Thr Arg Asn Arg Val Met Leu Glu Lys Ala Ser Ile Val Ser Gly Ala
            115                 120                 125
```

```
Thr Leu Ala Leu Leu Phe Met Ala Met Cys Cys Val Val Leu Tyr Leu
    130                 135                 140

Arg His Glu Lys Leu Gln Lys Gln Lys Leu His Asp Ser Thr Thr Thr
145                 150                 155                 160

Thr Thr Thr Asp Gly Gly Cys Gln Asn Glu Gly Met Asp Glu Val Asp
                165                 170                 175

Gly Leu Arg Pro Leu Arg Pro Val Arg Arg Pro Phe Gly Pro Cys Arg
            180                 185                 190

Ile Leu Ser Leu Glu Glu Ala His Leu Gln Ala Lys Ala Ser Asn Arg
        195                 200                 205

Pro Arg His Cys Asn Glu Leu Leu Arg
    210                 215

<210> SEQ ID NO 41
<211> LENGTH: 295
<212> TYPE: PRT
<213> ORGANISM: D. melanogaster

<400> SEQUENCE: 41

Met Met Gln Ile Pro Phe Thr Arg Ile Phe Lys Val Ile Phe Val Leu
  1               5                  10                  15

Ser Thr Ile Val Ala Val Thr Asp Cys Cys Ser Ser Arg Ile Leu Leu
             20                  25                  30

Leu Arg Glu His Thr Leu Lys Ile Val Gln His Gln His Ser His Met
         35                  40                  45

His Glu His Ala His Glu Leu Gln Gln Gln Ile Gln Glu Thr Ala Val
     50                  55                  60

Glu Leu Leu Asn Arg Leu Glu Leu Gln Arg Lys Gln Leu Glu Ala Ser
65                  70                  75                  80

Ala Gln Glu Glu Ala Asp Gln Leu His Pro Asp Thr Asp Pro Asn Pro
                 85                  90                  95

Asp Ser Gly Gly Gln Leu Pro Asn Ala Asp Asp Ser Ile Ala Ala Asp
            100                 105                 110

Pro Glu Gln Asp Gly Ile Ile Leu Gly Ser Ser Thr Asp Thr Trp Leu
        115                 120                 125

Ala Ser Glu Ser Ser Thr Pro Ile Thr Asp Ser Glu Thr Val Thr Thr
    130                 135                 140

Pro Glu Thr Val Thr His Thr Gly Glu Pro Pro Asp Pro Ser Ser
145                 150                 155                 160

Ser Ser Thr Pro Asp Ser Thr Thr Pro Ser Pro Asn Asp Lys Glu Thr
                165                 170                 175

Glu Ile Gln Met Leu Pro Cys Ser Glu Ala Tyr Asn Thr Ser Phe Cys
            180                 185                 190

Leu Asn Gly Gly His Cys Phe Gln His Pro Met Val Asn Asn Thr Val
        195                 200                 205

Phe His Ser Cys Leu Cys Val Asn Asp Tyr Asp Gly Glu Arg Cys Ala
    210                 215                 220

Tyr Lys Ser Trp Asn Gly Asp Tyr Ile Tyr Ser Pro Pro Thr Ala Gln
225                 230                 235                 240

Arg Lys Val Arg Met Ala His Ile Val Phe Ser Phe Pro Val Leu Leu
                245                 250                 255

Met Leu Ser Ser Leu Tyr Val Leu Phe Ala Ala Val Phe Met Leu Arg
            260                 265                 270

Asn Val Pro Asp Tyr Arg Arg Lys Gln Gln Gln Leu His Leu His Lys
        275                 280                 285
```

```
Gln Arg Phe Phe Val Arg Cys
    290             295

<210> SEQ ID NO 42
<211> LENGTH: 160
<212> TYPE: PRT
<213> ORGANISM: H. sapiens

<400> SEQUENCE: 42

Met Val Pro Ser Ala Gly Gln Leu Ala Leu Phe Ala Leu Gly Ile Val
 1               5                  10                  15

Leu Ala Ala Cys Gln Ala Leu Glu Asn Ser Thr Ser Pro Leu Ser Ala
                20                  25                  30

Asp Pro Pro Val Ala Ala Val Val Ser His Phe Asn Asp Cys Pro
            35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
 65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
        115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145                 150                 155                 160

<210> SEQ ID NO 43
<211> LENGTH: 1210
<212> TYPE: PRT
<213> ORGANISM: H. sapiens

<400> SEQUENCE: 43

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160
```

-continued

```
Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575
```

-continued

```
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
```

-continued

```
                995                 1000                1005
Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
        1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
        1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
        1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

<210> SEQ ID NO 44
<211> LENGTH: 208
<212> TYPE: PRT
<213> ORGANISM: H. sapiens

<400> SEQUENCE: 44

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160
```

```
Thr Ile Leu Ala Val Val Ala Val Val Leu Ser Ser Val Cys Leu Leu
            165                 170                 175

Val Ile Val Gly Leu Leu Met Phe Arg Tyr His Arg Arg Gly Gly Tyr
        180                 185                 190

Asp Val Glu Asn Glu Glu Lys Val Lys Leu Gly Met Thr Asn Ser His
            195                 200                 205

<210> SEQ ID NO 45
<211> LENGTH: 178
<212> TYPE: PRT
<213> ORGANISM: H. sapiens

<400> SEQUENCE: 45

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
            20                  25                  30

Gly Asn Ser Thr Arg Ser Pro Glu Thr Asn Gly Leu Leu Cys Gly Asp
        35                  40                  45

Pro Glu Glu Asn Cys Ala Ala Thr Thr Thr Gln Ser Lys Arg Lys Gly
    50                  55                  60

His Phe Ser Arg Cys Pro Lys Gln Tyr Lys His Tyr Cys Ile Lys Gly
65                  70                  75                  80

Arg Cys Arg Phe Val Val Ala Glu Gln Thr Pro Ser Cys Val Cys Asp
                85                  90                  95

Glu Gly Tyr Ile Gly Ala Arg Cys Glu Arg Val Asp Leu Phe Tyr Leu
            100                 105                 110

Arg Gly Asp Arg Gly Gln Ile Leu Val Ile Cys Leu Ile Ala Val Met
        115                 120                 125

Val Val Phe Ile Ile Leu Val Ile Gly Val Cys Thr Cys Cys His Pro
    130                 135                 140

Leu Arg Lys Arg Arg Lys Arg Lys Lys Glu Glu Glu Met Glu Thr
145                 150                 155                 160

Leu Gly Lys Asp Ile Thr Pro Ile Asn Glu Asp Ile Glu Glu Thr Asn
                165                 170                 175

Ile Ala

<210> SEQ ID NO 46
<211> LENGTH: 252
<212> TYPE: PRT
<213> ORGANISM: H. sapiens

<400> SEQUENCE: 46

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
```

```
                100             105             110
Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
        180                 185                 190

Asp Ser Ser Leu Ser Lys Ile Ala Leu Ala Ala Ile Ala Ala Phe Met
                195                 200                 205

Ser Ala Val Ile Leu Thr Ala Val Ala Val Ile Thr Val Gln Leu Arg
        210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 47
<211> LENGTH: 169
<212> TYPE: PRT
<213> ORGANISM: H. sapiens

<400> SEQUENCE: 47

Met Thr Ala Gly Arg Arg Met Glu Met Leu Cys Ala Gly Arg Val Pro
  1               5                  10                  15

Ala Leu Leu Leu Cys Leu Gly Phe His Leu Leu Gln Ala Val Leu Ser
                 20                  25                  30

Thr Thr Val Ile Pro Ser Cys Ile Pro Gly Glu Ser Ser Asp Asn Cys
             35                  40                  45

Thr Ala Leu Val Gln Thr Glu Asp Asn Pro Arg Val Ala Gln Val Ser
         50                  55                  60

Ile Thr Lys Cys Ser Ser Asp Met Asn Gly Tyr Cys Leu His Gly Gln
 65                  70                  75                  80

Cys Ile Tyr Leu Val Asp Met Ser Gln Asn Tyr Cys Arg Cys Glu Val
                 85                  90                  95

Gly Tyr Thr Gly Val Arg Cys Glu His Phe Phe Leu Thr Val His Gln
            100                 105                 110

Pro Leu Ser Lys Glu Tyr Val Ala Leu Thr Val Ile Leu Ile Ile Leu
        115                 120                 125

Phe Leu Ile Thr Val Val Gly Ser Thr Tyr Tyr Phe Cys Arg Trp Tyr
130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
                165

<210> SEQ ID NO 48
<211> LENGTH: 438
<212> TYPE: PRT
<213> ORGANISM: C. elegans

<400> SEQUENCE: 48

Met Arg Lys Met Leu Leu Phe Cys Ile Leu Leu Leu Phe Met Pro Gln
```

-continued

```
  1               5                  10                 15
Phe Thr Val Ser Glu Ser Cys Leu Pro Ser Trp Phe Arg Gln Glu Arg
             20                  25                  30

Ser Ala Pro Glu Gln Leu Gln Ser Ala Glu Asn Ala Ala Glu Asn Ser
             35                  40                  45

Gly Ser Val Pro Pro Asp Thr Ser Arg Asn Ser Leu Glu Thr Asn Glu
 50                  55                  60

Ile Gly Asp Ala Pro Ser Ser Thr Ser Thr Pro Glu Thr Pro Thr Glu
 65                  70                  75                  80

Thr Thr Ile Ser Glu Ala Gly Asp Asp Lys Arg Thr Glu Glu Val
                 85                  90                  95

Ala Lys Glu Leu Ile Glu Lys Glu Ala Glu Tyr Glu Gly Glu Tyr Glu
                100                 105                 110

Asp Glu Lys Val Asp Glu Glu Val Glu Glu Ala Leu Lys Tyr Asn Glu
                115                 120                 125

Asp Ala Thr Gln Asp Ala Thr Ser Thr Leu Lys Pro Ala Val Arg Lys
            130                 135                 140

Glu Ile Glu Lys Leu Lys Glu Ala Lys Cys Lys Asp Tyr Cys His His
145                 150                 155                 160

Asn Ala Thr Cys His Val Glu Val Ile Phe Arg Glu Asp Arg Val Ser
                165                 170                 175

Ala Val Val Pro Ser Cys His Cys Pro Gln Gly Trp Glu Gly Thr Arg
                180                 185                 190

Cys Asp Arg His Tyr Val Gln Ala Phe Tyr Ala Pro Ile Asn Gly Arg
            195                 200                 205

Tyr Asn Val Arg Leu Ser Thr Met Ser Ser Thr Ala Gln Leu Leu Val
        210                 215                 220

Gln Gln Ser Ser Thr Ser Ala Ile Pro Ala Phe Ala Phe Leu Ile Val
225                 230                 235                 240

Met Leu Ile Met Phe Ile Thr Ile Val Val Tyr Ala Tyr Arg Arg Met
                245                 250                 255

Ser Lys Arg Ser Asp Asp Met Thr Tyr Thr Met Ser His Met Cys Pro
                260                 265                 270

Pro Glu Ala Phe Asn Val Leu Lys Thr Pro Asn Gly Arg His Ile Pro
            275                 280                 285

Val His Gln Ile Pro Ser Cys Ser Tyr Thr Ile Pro Thr Pro Gly Thr
        290                 295                 300

Val Pro Pro Asn Ile Ser Ser Thr Pro Gly Ser Arg Ile Pro Thr Arg
305                 310                 315                 320

Gln Gln Ala Ile Arg Asn Asn Glu Gln Ala Arg Asn Asn Phe Phe Ser
                325                 330                 335

Ile Leu Arg Ser Gln Gly Thr Ile Pro Ser Arg Ser Ile Asn Asp Asp
            340                 345                 350

Asp Thr Pro Lys His Tyr Lys Ser Val Pro Arg Val Glu Val Ser Ala
        355                 360                 365

Ile Asn Tyr Ser Gly His Ile Asp Phe Ser Thr Val Ser Tyr Gln Ser
        370                 375                 380

Thr Glu Ser Glu Val Ser Lys Ala Ser Val Thr Cys Pro Pro Pro Ala
385                 390                 395                 400
```

```
                        -continued
His Thr Val Ile Asn Ile Glu Leu Asp Ser Ala Asp Thr Asn Phe Arg
                405             410             415

Ser Pro Ser Arg Ser Ser Gly Glu Gln Gly Ser Pro Ala Thr Cys Glu
            420             425             430

Pro Met Ile Arg His Thr
            435
```